US009783596B2

(12) United States Patent
Goncalvez et al.

(10) Patent No.: US 9,783,596 B2
(45) Date of Patent: *Oct. 10, 2017

(54) HUMANIZED MONOCLONAL ANTIBODIES THAT SPECIFICALLY BIND AND/OR NEUTRALIZE JAPANESE ENCEPHALITIS VIRUS (JEV) AND THEIR USE

(71) Applicant: THE UNITED STATES OF AMERICA, as represented by the Secretary, Department of Health and Human Services, Washington, DC (US)

(72) Inventors: Ana P. Goncalvez, Watertown, MA (US); Robert H. Purcell, Gaithersburg, MD (US); Ching-Juh Lai, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/004,795

(22) Filed: Jan. 22, 2016

(65) Prior Publication Data

US 2016/0137722 A1    May 19, 2016

Related U.S. Application Data

(63) Continuation of application No. 13/941,283, filed on Jul. 12, 2013, now Pat. No. 9,273,121, which is a continuation of application No. 12/937,227, filed as application No. PCT/US2009/040227 on Apr. 10, 2009, now Pat. No. 8,506,961.

(60) Provisional application No. 61/123,905, filed on Apr. 10, 2008.

(51) Int. Cl.
  *C07K 16/10*       (2006.01)
  *G01N 33/569*      (2006.01)
  *A61K 47/48*       (2006.01)
  *A61K 39/00*       (2006.01)

(52) U.S. Cl.
  CPC ...... *C07K 16/1081* (2013.01); *A61K 47/4853* (2013.01); *C07K 16/10* (2013.01); *G01N 33/569* (2013.01); *G01N 33/56983* (2013.01); *A61K 2039/505* (2013.01); *A61K 2039/507* (2013.01); *C07K 2317/21* (2013.01); *C07K 2317/24* (2013.01); *C07K 2317/51* (2013.01); *C07K 2317/515* (2013.01); *C07K 2317/52* (2013.01); *C07K 2317/524* (2013.01); *C07K 2317/526* (2013.01); *C07K 2317/55* (2013.01); *C07K 2317/76* (2013.01); *C07K 2317/92* (2013.01); *G01N 2333/185* (2013.01)

(58) Field of Classification Search
  None
  See application file for complete search history.

(56) References Cited

PUBLICATIONS

Goncalvez et al., "Humanized Monoclonal Antibodies Derived from Chimpanzee Fabs Protect Against Japanese Encephalitis Virus In Vitro and In Vivo," *Journal of Virology* 82(14):7009-7021 (Jul. 2008).
International Search Report and Written Opinion from parent PCT Application No. PCl/US2009/040227, 5 pages (mailed Dec. 28, 2009).
Kimura-Kuroda and Yasui "Protection of Mice Against Japanese Encephalitis Virus by Passive Administration with Monoclonal Antibodies," *Journal of Immunology* 141(10):3606-3610 (Nov. 15, 1988).
Kimura-Kuroda and Yasui "Topographical Analysis of Antigenic Determinants on Envelope Glycoprotein V3 (E) of Japanese Encephalitis Virus, Using Monoclonal Antibodies," *Journal of Virology* 45(1):124-132 (Jan. 1983).
Lin and Wu, "A Functional Epitope Determinant on Domain III of the Japanese Encephalitis Virus Protein Interacted with Neutralizing-Antibody Combining Sites," *Journal of Virology* 77(4):2600-2606 (Feb. 2003).
Wu et al., Japanese Encephalitis Virus Antigenic Variants with Characteristic Differences in Neutralization Resistance and Mouse Virulence, *Virus Research* 51:173-181 (1997).

*Primary Examiner* — Laura B Goddard
*Assistant Examiner* — Meera Natarajan
(74) *Attorney, Agent, or Firm* — Klarquist Sparkman, LLP

(57) ABSTRACT

Disclosed herein are isolated humanized monoclonal antibodies that specifically bind Japanese encephalitis virus (JEV) with a binding affinity of about 1.0 nM or less. Nucleic acids encoding these antibodies, expression vectors including these nucleic acid molecules, and isolated host cells that express the nucleic acid molecules are also disclosed. Methods of treating, preventing, and/or ameliorating JEV infection in a subject with JEV also are disclosed. Additionally, the antibodies can be used to detect JEV in a sample, and methods of diagnosing JEV infection, or confirming a diagnosis of JEV infection in a subject, are disclosed herein that utilize these antibodies.

24 Claims, 9 Drawing Sheets

SEQUENCE LISTING

<160> NUMBER OF SEQ ID NOS: 36

<210> SEQ ID NO 1
<211> LENGTH: 119
<212> TYPE: PRT
<213> ORGANISM: Artificial sequence
<220> FEATURE:
<223> OTHER INFORMATION: Recombinantly produced heavy chain of
      monoclonal antibody A3

<400> SEQUENCE: 1

Glu Val Gln Leu Leu Glu Ser Gly Ala Glu Val Lys Lys Pro Gly Ser
1               5                   10                  15

Ser Val Arg Ile Ser Cys Lys Val Ser Gly Thr Pro Tyr Ser Ser Tyr
            20                  25                  30

Val Met Asn Trp Val Arg Gln Ala Pro Gly Gln Gly Leu Glu Trp Met
        35                  40                  45

Gly Val Phe Val Pro Ser Leu Asp Arg Ala Leu Tyr Ala Gln Asn Phe

```
                  50                  55                  60
Gln Gly Arg Leu Ser Ile Thr Ala Asp Thr Thr Thr Thr Tyr Met Glu
 65                  70                  75                  80

Leu Thr Ser Leu Lys Phe Glu Asp Thr Ala Val Tyr Tyr Cys Ala Thr
                 85                  90                  95

Asp Phe Ser Val Gly Trp Leu Arg Pro Leu Asp Arg Trp Gly Gln Gly
                100                 105                 110

Thr Leu Val Thr Val Ser Ser
        115

<210> SEQ ID NO 2
<211> LENGTH: 124
<212> TYPE: PRT
<213> ORGANISM: Artificial sequence
<220> FEATURE:
<223> OTHER INFORMATION: Recombinantly produced heavy chain of
      monoclonal antibody B2

<400> SEQUENCE: 2

Glu Val Gln Leu Leu Glu Gln Ser Gly Ser Glu Val Lys Lys Pro Gly
 1               5                  10                  15

Ala Ser Val Lys Val Ser Cys Lys Ala Ser Gly Tyr Pro Phe Thr Asp
                 20                  25                  30

Tyr Ala Met Ser Trp Val Arg Gln Ala Pro Gly Gln Gly Leu Glu Tyr
             35                  40                  45

Met Gly Trp Ile Phe Thr Asn Ser Gly Asn Pro Thr Tyr Ala Pro Gly
         50                  55                  60

Phe Ala Gly Arg Phe Val Phe Ser Leu Asp Ile Ser Val Asn Thr Ala
 65                  70                  75                  80

Tyr Leu His Ile Asp Ser Leu Lys Pro Glu Asp Thr Ala Val Tyr Tyr
                 85                  90                  95

Cys Ala Arg Gly Ile Val Thr Pro Ala Ala Ser Gly Asp Tyr Phe Asp
                100                 105                 110

Ser Trp Gly Gln Gly Thr Leu Val Thr Val Ser Ser
        115                 120

<210> SEQ ID NO 3
<211> LENGTH: 123
<212> TYPE: PRT
<213> ORGANISM: Artificial sequence
<220> FEATURE:
<223> OTHER INFORMATION: Recombinantly produced heavy chain of
      monoclonal antibody E3

<400> SEQUENCE: 3

Glu Val Gln Leu Leu Glu Ser Gly Pro Gly Leu Val Arg Pro Ser Gln
 1               5                  10                  15

Thr Leu Ser Leu Thr Cys Ala Val Ser Gly Ala Ser Ile Ser Gly Pro
                 20                  25                  30

Leu Ser Tyr Trp Thr Trp Ile Arg Gln Ser Pro Gly Lys Lys Met Glu
             35                  40                  45

His Ile Gly Ser Met Phe Tyr Ser Gly Asn Thr Tyr Tyr Asn Pro Ser
         50                  55                  60

Leu Lys Gly Arg Ile Thr Met Ser Val Asp Thr Ser Arg Asn Gln Phe
 65                  70                  75                  80

Ser Leu Asn Leu Asn Ser Val Thr Val Ala Asp Thr Ala Val Tyr Phe
                 85                  90                  95

Cys Ala Arg Arg Arg Glu Thr Glu Leu Phe Gly Leu Pro Ile Asp Tyr
```

```
                100               105                110
Trp Gly Gln Gly Ile Leu Val Thr Val Ser Ser
        115                 120

<210> SEQ ID NO 4
<211> LENGTH: 109
<212> TYPE: PRT
<213> ORGANISM: Artificial sequence
<220> FEATURE:
<223> OTHER INFORMATION: Recombinantly produced light chain of
      monoclonal antibody A3

<400> SEQUENCE: 4

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Ala Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Ser Asn Pro Phe
                85                  90                  95

Thr Phe Gly Pro Gly Thr Lys Val Asp Ile Lys Arg Thr
            100                 105

<210> SEQ ID NO 5
<211> LENGTH: 109
<212> TYPE: PRT
<213> ORGANISM: Artificial sequence
<220> FEATURE:
<223> OTHER INFORMATION: Recombinantly produced light chain of
      monoclonal antibody B2

<400> SEQUENCE: 5

Glu Leu Val Leu Thr Gln Ser Pro Ser Ser Leu Ser Ala Ser Ile Gly
1               5                   10                  15

Asp Arg Val Thr Ile Thr Cys Arg Ala Ser Gln His Ile Ser Ser Trp
            20                  25                  30

Leu Ala Trp Tyr Gln Gln Lys Pro Gly Lys Ala Pro Lys Pro Leu Ile
        35                  40                  45

Tyr Ala Ala Ser Ser Leu Lys Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Tyr Glu Asn Ser Pro Val
                85                  90                  95

Thr Phe Gly Gly Gly Thr Lys Val Glu Ile Lys Arg Thr
            100                 105

<210> SEQ ID NO 6
<211> LENGTH: 108
<212> TYPE: PRT
<213> ORGANISM: Artificial Sequence
<220> FEATURE:
<223> OTHER INFORMATION: Recombinantly produced light chain of
      monoclonal antibody E3

<400> SEQUENCE: 6
```

Glu Leu Thr Gln Ser Pro Ala Thr Leu Ser Val Ser Pro Gly Glu Arg
1               5                   10                  15

Ala Thr Leu Ser Cys Arg Ala Ser Glu Arg Ile Ser Ser Tyr Leu
            20                  25                  30

Ser Trp Tyr Gln Gln Lys Pro Gly Gln Ala Pro Arg Leu Leu Met Tyr
                35                  40                  45

Gly Thr Ser Thr Arg Ala Thr Gly Ile Pro Ala Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Val Tyr Phe Cys Gln Gln Asp Tyr Asn Leu Pro Trp Thr
                85                  90                  95

Phe Gly Gln Gly Thr Lys Leu Glu Ile Lys Arg Thr
                100                 105

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide primer.

<400> SEQUENCE: 7
ggagccatga agagatctaa tttccagggg                                      30

<210> SEQ ID NO 8
<211> LENGTH: 33
<212> TYPE: DNA
<213> ORGANISM: Artificial sequence
<220> FEATURE:
<223> OTHER INFORMATION: Synthetic oligonucleotide primer.

<400> SEQUENCE: 8
gcccagcgtg ctccgcggtt tgtgccaatg gtg                                  33

<210> SEQ ID NO 9
<211> LENGTH: 900
<212> TYPE: DNA
<213> ORGANISM: Japanese encephalitis virus

<400> SEQUENCE: 9
tttaattgtc tgggaatggg caatcgtgac ttcatagaag gagccagtgg agccacttgg     60
gtggacttgg tgctagaagg agacagctgc ttgacaatca tggcaaacga caaaccaaca    120
ttggacgtcc gcatgattaa catcgaagct agccaacttg ctgaggtcag aagttactgc    180
tatcatgctt cagtcactga catctcgacg gtggctcggt gccccacgac tggagaagcc    240
cacaacgaga agcgagctga tagtagctat gtgtgcaaac aaggcttcac tgaccgtggg    300
tggggcaacg gatgtggatt tttcgggaag ggaagcattg acacatgtgc aaaattctcc    360
tgcaccagta aagcgattgg gagaacaatc cagccagaaa acatcaaata caaagttggc    420 attttgtgc atggaaccac cacttcggaa accatggga attattcagc gcaagttggg    480
gcgtcccagg cggcaaagtt tacagtaaca cccaatgctc cttcggtagc cctcaaactt    540
ggtgactacg gagaagtcac actggactgt gagccaagga gtggactgaa cactgaagcg    600
ttttacgtca tgaccgtggg gtcaaagtca tttctggtcc atagggagtg gtttcatgac    660
ctcgctctcc cctggacgtc cccttcgagc acagcgtgga gaaacagaga actcctcatg    720
gaatttgaag gggcgcacgc cacaaaacag tccgttgttg ctcttgggtc acaggaagga    780

```
ggcctccatc atgcgttggc aggagccatc gtggtggagt actcaagctc agtgatgtta    840
acatcaggcc acctgaaatg taggctgaaa atggacaaac tggctctgaa aggcacaacc    900
```

<210> SEQ ID NO 10
<211> LENGTH: 499
<212> TYPE: PRT
<213> ORGANISM: Japanese encephalitis virus

<400> SEQUENCE: 10

```
Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Phe Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Lys Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Val
                165                 170                 175

Ala Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Gly Ala His Ala Thr Lys Gln Ser Val Val Ala Leu Gly
                245                 250                 255

Ser Gln Glu Gly Gly Leu His His Ala Leu Ala Gly Ala Ile Val Glu
            260                 265                 270

Tyr Ser Ser Ser Val Met Leu Thr Ser Gly His Leu Lys Cys Arg Leu
        275                 280                 285

Lys Met Asp Lys Leu Ala Leu Lys Gly Thr Thr Tyr Gly Met Cys Thr
    290                 295                 300

Glu Lys Phe Ser Phe Ala Lys Asn Pro Val Asp Thr Gly His Gly Thr
305                 310                 315                 320

Val Val Ile Glu Leu Ser Tyr Ser Gly Ser Asp Gly Pro Cys Lys Ile
                325                 330                 335

Pro Ile Val Ser Val Ala Ser Leu Asn Asp Met Thr Pro Val Gly Arg
            340                 345                 350
```

-continued

Leu Val Thr Val Asn Pro Phe Val Ala Thr Ser Ser Ala Asn Ser Lys
355                 360                 365

Val Leu Val Glu Met Glu Pro Pro Phe Gly Asp Ser Tyr Ile Val Val
370                 375                 380

Gly Arg Gly Asp Lys Gln Ile Asn His His Trp His Lys Ala Gly Ser
385                 390                 395                 400

Thr Leu Gly Lys Ala Phe Ser Thr Thr Leu Lys Gly Ala Gln Arg Leu
        405                 410                 415

Ala Ala Leu Gly Asp Thr Ala Trp Asp Phe Gly Ser Ile Gly Gly Val
            420                 425                 430

Phe Asn Ser Ile Gly Arg Ala Val His Gln Val Phe Gly Asp Ala Phe
        435                 440                 445

Arg Thr Leu Phe Gly Gly Met Ser Trp Ile Thr Gln Gly Leu Met Gly
    450                 455                 460

Ala Leu Leu Leu Trp Met Gly Val Asn Ala Arg Asp Arg Ser Ile Ala
465                 470                 475                 480

Leu Ala Phe Leu Ala Thr Gly Gly Val Leu Val Phe Leu Ala Thr Asn
            485                 490                 495

Val His Ala

<210> SEQ ID NO 11
<211> LENGTH: 330
<212> TYPE: PRT
<213> ORGANISM: Artificial sequence
<220> FEATURE:
<223> OTHER INFORMATION: Recombinantly produced heavy chain of
      monoclonal antibody A3

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asp His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 4
<212> TYPE: PRT
<213> ORGANISM: Homo sapiens

<400> SEQUENCE: 12

Leu Leu Gly Gly
1

<210> SEQ ID NO 13
<211> LENGTH: 5
<212> TYPE: PRT
<213> ORGANISM: Artificial sequence
<220> FEATURE:
<223> OTHER INFORMATION: Recombinantly produced heavy chain of
      monoclonal antibody A3

<400> SEQUENCE: 13

Glu Leu Leu Gly Gly
1               5

<210> SEQ ID NO 14
<211> LENGTH: 5
<212> TYPE: PRT
<213> ORGANISM: Homo sapiens

<400> SEQUENCE: 14

Leu Leu Gly Gly Pro
1               5

<210> SEQ ID NO 15
<211> LENGTH: 6
<212> TYPE: PRT
<213> ORGANISM: Homo sapiens

<400> SEQUENCE: 15

Pro Glu Leu Leu Gly Gly
1               5

<210> SEQ ID NO 16
<211> LENGTH: 6
<212> TYPE: PRT
<213> ORGANISM: Homo sapiens

<400> SEQUENCE: 16
```

```
Glu Leu Leu Gly Gly Pro
1               5

<210> SEQ ID NO 17
<211> LENGTH: 6
<212> TYPE: PRT
<213> ORGANISM: Homo sapiens

<400> SEQUENCE: 17

Leu Leu Gly Gly Pro Ser
1               5

<210> SEQ ID NO 18
<211> LENGTH: 7
<212> TYPE: PRT
<213> ORGANISM: Homo sapiens

<400> SEQUENCE: 18

Ala Pro Glu Leu Leu Gly Gly
1               5

<210> SEQ ID NO 19
<211> LENGTH: 7
<212> TYPE: PRT
<213> ORGANISM: Homo sapiens

<400> SEQUENCE: 19

Pro Glu Leu Leu Gly Gly Pro
1               5

<210> SEQ ID NO 20
<211> LENGTH: 7
<212> TYPE: PRT
<213> ORGANISM: Homo sapiens

<400> SEQUENCE: 20

Glu Leu Leu Gly Gly Pro Ser
1               5

<210> SEQ ID NO 21
<211> LENGTH: 7
<212> TYPE: PRT
<213> ORGANISM: Homo sapiens

<400> SEQUENCE: 21

Leu Leu Gly Gly Pro Ser Val
1               5

<210> SEQ ID NO 22
<211> LENGTH: 8
<212> TYPE: PRT
<213> ORGANISM: Homo sapiens

<400> SEQUENCE: 22

Pro Ala Pro Glu Leu Leu Gly Gly
1               5

<210> SEQ ID NO 23
<211> LENGTH: 8
<212> TYPE: PRT
<213> ORGANISM: Homo sapiens

<400> SEQUENCE: 23

Ala Pro Glu Leu Leu Gly Gly Pro
1               5
```

<210> SEQ ID NO 24
<211> LENGTH: 8
<212> TYPE: PRT
<213> ORGANISM: Artificial sequence
<220> FEATURE:
<223> OTHER INFORMATION: Recombinantly produced heavy chain of
      monoclonal antibody A3

<400> SEQUENCE: 24

Pro Glu Leu Leu Gly Gly Pro Ser
1               5

<210> SEQ ID NO 25
<211> LENGTH: 8
<212> TYPE: PRT
<213> ORGANISM: Homo sapiens

<400> SEQUENCE: 25

Glu Leu Leu Gly Gly Pro Ser Val
1               5

<210> SEQ ID NO 26
<211> LENGTH: 9
<212> TYPE: PRT
<213> ORGANISM: Homo sapiens

<400> SEQUENCE: 26

Pro Ala Pro Glu Leu Leu Gly Gly Pro
1               5

<210> SEQ ID NO 27
<211> LENGTH: 9
<212> TYPE: PRT
<213> ORGANISM: Homo sapiens

<400> SEQUENCE: 27

Ala Pro Glu Leu Leu Gly Gly Pro Ser
1               5

<210> SEQ ID NO 28
<211> LENGTH: 9
<212> TYPE: PRT
<213> ORGANISM: Artificial sequence
<220> FEATURE:
<223> OTHER INFORMATION: Recombinantly produced heavy chain of
      monoclonal antibody A3

<400> SEQUENCE: 28

Pro Glu Leu Leu Gly Gly Pro Ser Val
1               5

<210> SEQ ID NO 29
<211> LENGTH: 10
<212> TYPE: PRT
<213> ORGANISM: Homo sapiens

<400> SEQUENCE: 29

Pro Ala Pro Glu Leu Leu Gly Gly Pro Ser
1               5                   10

<210> SEQ ID NO 30
<211> LENGTH: 10
<212> TYPE: PRT
<213> ORGANISM: Homo sapiens

<400> SEQUENCE: 30

Ala Pro Glu Leu Leu Gly Gly Pro Ser Val
1               5                   10

<210> SEQ ID NO 31
<211> LENGTH: 449
<212> TYPE: PRT
<213> ORGANISM: Artificial sequence
<220> FEATURE:
<223> OTHER INFORMATION: Recombinantly produced heavy chain of
      monoclonal antibody A3

<400> SEQUENCE: 31

Glu Val Gln Leu Leu Glu Ser Gly Ala Glu Val Lys Lys Pro Gly Ser
1               5                   10                  15

Ser Val Arg Ile Ser Cys Lys Val Ser Gly Thr Pro Tyr Ser Ser Tyr
            20                  25                  30

Val Met Asn Trp Val Arg Gln Ala Pro Gly Gln Gly Leu Glu Trp Met
        35                  40                  45

Gly Val Phe Val Pro Ser Leu Asp Arg Ala Leu Tyr Ala Gln Asn Phe
    50                  55                  60

Gln Gly Arg Leu Ser Ile Thr Ala Asp Thr Thr Thr Thr Tyr Met Glu
65                  70                  75                  80

Leu Thr Ser Leu Lys Phe Glu Asp Thr Ala Val Tyr Tyr Cys Ala Thr
                85                  90                  95

Asp Phe Ser Val Gly Trp Leu Arg Pro Leu Asp Arg Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asp His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Pro Val Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

-continued

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 32
<211> LENGTH: 454
<212> TYPE: PRT
<213> ORGANISM: Artificial sequence
<220> FEATURE:
<223> OTHER INFORMATION: Recombinantly produced heavy chain of
      monoclonal antibody B2

<400> SEQUENCE: 32

Glu Val Gln Leu Leu Glu Gln Ser Gly Ser Glu Val Lys Lys Pro Gly
1               5                   10                  15

Ala Ser Val Lys Val Ser Cys Lys Ala Ser Gly Tyr Pro Phe Thr Asp
                20                  25                  30

Tyr Ala Met Ser Trp Val Arg Gln Ala Pro Gly Gln Gly Leu Glu Tyr
            35                  40                  45

Met Gly Trp Ile Phe Thr Asn Ser Gly Asn Pro Thr Tyr Ala Pro Gly
        50                  55                  60

Phe Ala Gly Arg Phe Val Phe Ser Leu Asp Ile Ser Val Asn Thr Ala
65                  70                  75                  80

Tyr Leu His Ile Asp Ser Leu Lys Pro Glu Asp Thr Ala Val Tyr Tyr
                85                  90                  95

Cys Ala Arg Gly Ile Val Thr Pro Ala Ala Ser Gly Asp Tyr Phe Asp
                100                 105                 110

Ser Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asp His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Pro
225                 230                 235                 240
```

```
Val Glu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 33
<211> LENGTH: 453
<212> TYPE: PRT
<213> ORGANISM: Artificial sequence
<220> FEATURE:
<223> OTHER INFORMATION: Recombinantly produced heavy chain of
      monoclonal antibody E3

<400> SEQUENCE: 33

Glu Val Gln Leu Leu Glu Ser Gly Pro Gly Leu Val Arg Pro Ser Gln
1               5                   10                  15

Thr Leu Ser Leu Thr Cys Ala Val Ser Gly Ala Ser Ile Ser Gly Pro
            20                  25                  30

Leu Ser Tyr Trp Thr Trp Ile Arg Gln Ser Pro Gly Lys Lys Met Glu
        35                  40                  45

His Ile Gly Ser Met Phe Tyr Ser Gly Asn Thr Tyr Tyr Asn Pro Ser
    50                  55                  60

Leu Lys Gly Arg Ile Thr Met Ser Val Asp Thr Ser Arg Asn Gln Phe
65                  70                  75                  80

Ser Leu Asn Leu Asn Ser Val Thr Val Ala Asp Thr Ala Val Tyr Phe
                85                  90                  95

Cys Ala Arg Arg Arg Glu Thr Glu Leu Phe Gly Leu Pro Ile Asp Tyr
            100                 105                 110

Trp Gly Gln Gly Ile Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asp His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Pro Val
225                 230                 235                 240

Glu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 34
<211> LENGTH: 210
<212> TYPE: PRT
<213> ORGANISM: Artificial sequence
<220> FEATURE:
<223> OTHER INFORMATION: Recombinantly produced light chain of
      monoclonal antibody A3

<400> SEQUENCE: 34

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
```

```
                  35                  40                  45
Tyr Tyr Ala Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Tyr Asn Ser Asn Pro Phe
                 85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Asn Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn
    210

<210> SEQ ID NO 35
<211> LENGTH: 210
<212> TYPE: PRT
<213> ORGANISM: Artificial sequence
<220> FEATURE:
<223> OTHER INFORMATION: Recombinantly produced light chain of
      monoclonal antibody B2

<400> SEQUENCE: 35

Glu Leu Val Leu Thr Gln Ser Pro Ser Ser Leu Ser Ala Ser Ile Gly
 1               5                  10                  15

Asp Arg Val Thr Ile Thr Cys Arg Ala Ser Gln His Ile Ser Ser Trp
                 20                  25                  30

Leu Ala Trp Tyr Gln Gln Lys Pro Gly Lys Ala Pro Lys Pro Leu Ile
             35                  40                  45

Tyr Ala Ala Ser Ser Leu Lys Ser Gly Val Pro Ser Arg Phe Ser Gly
 50                  55                  60

Ser Gly Ser Gly Thr Asp Phe Thr Leu Thr Ile Ser Gly Leu Gln Pro
 65                  70                  75                  80

Glu Asp Phe Ala Thr Tyr Tyr Cys Gln Gln Tyr Glu Asn Ser Pro Val
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Asn Thr Tyr Ser Leu Ser
                165                 170                 175
```

```
Ser Thr Leu Thr Leu Ser Lys Ala Asp Tyr Glu Lys His Lys Val Tyr
            180             185                 190

Ala Cys Glu Val Thr His Gln Gly Leu Ser Ser Pro Val Thr Lys Ser
        195                 200                 205

Phe Asn
    210

<210> SEQ ID NO 36
<211> LENGTH: 209
<212> TYPE: PRT
<213> ORGANISM: Artificial sequence
<220> FEATURE:
<223> OTHER INFORMATION: Recombinantly produced light chain of
      monoclonal antibody E3

<400> SEQUENCE: 36

Glu Leu Thr Gln Ser Pro Ala Thr Leu Ser Val Ser Pro Gly Glu Arg
1               5                   10                  15

Ala Thr Leu Ser Cys Arg Ala Ser Glu Arg Ile Ser Ser Ser Tyr Leu
            20                  25                  30

Ser Trp Tyr Gln Gln Lys Pro Gly Gln Ala Pro Arg Leu Leu Met Tyr
        35                  40                  45

Gly Thr Ser Thr Arg Ala Thr Gly Ile Pro Ala Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Val Tyr Phe Cys Gln Gln Asp Tyr Asn Leu Pro Trp Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn
```

HUMANIZED MONOCLONAL ANTIBODIES THAT SPECIFICALLY BIND AND/OR NEUTRALIZE JAPANESE ENCEPHALITIS VIRUS (JEV) AND THEIR USE

CROSS REFERENCE TO RELATED REFERENCES

This is a continuation of U.S. patent application Ser. No. 13/941,283, filed Jul. 12, 2013, which is a continuation of U.S. patent application Ser. No. 12/937,227, filed Oct. 8, 2010, issued as U.S. Pat. No. 8,506,961, which is the U.S. national stage of PCT Application No. PCT/US2009/040227, filed Apr. 10, 2009, which was published in English under PCT Article 21(2), which in turn claims the benefit of U.S. Provisional Application No. 61/123,905, filed on Apr. 10, 2008. The prior applications are incorporated herein by reference their entirety.

FIELD

This disclosure is related to humanized monoclonal antibodies, specifically to humanized monoclonal antibodies that specifically bind Japanese encephalitis virus (JEV), and their use.

BACKGROUND

Japanese encephalitis virus (JEV) is the prototype virus of the Japanese encephalitis (JE) group belonging to the Flavivirus genus of the Flaviviridae family. Other members of the group include Kunjin virus, St. Louis encephalitis virus (SLEV) and West Nile encephalitis virus (WNV). JEV is widely distributed in South Asia, Southeast Asia, and the Asian Pacific Rim. In recent years, JE epidemics have spread to previously unaffected areas, such as northern Australia (Hanna, et al. (1996) *Med J Aust* 165:256-60; Pyke, et al. (2001) *Am J Trop Med Hyg* 65:747-53), Pakistan (Igarashi, et al. (1994) *Microbiol Immunol* 38:827-30), India and Indonesia (Mackenzie, et al. (2004) *Nat Med* 10:S98-109). The JE outbreak in India during July-November of 2005 was the longest and most severe in recent years, affecting in excess of 5,000 persons and causing greater than 1,000 deaths (Parida, et al. (2006) *Emerg Infect Dis* 12:1427-30).

It is estimated that JEV causes 35,000-50,000 cases of encephalitis, including 10,000 deaths and as many neurologic sequelae each year (Tsai (2000) *Vaccine* 18 Suppl 2:1-25). Although only one JEV serotype is known to exist, cross-neutralization experiments have demonstrated antigenic differences among JEV strains (Ali & Igarashi (1997) *Microbiol Immunol* 41:241-52). Phylogenic studies have identified five JEV genotypes, four of which are presently recognized (Chen, et al. (1992) *Am J Trop Med Hyg* 47:61-9; Solomon, et al. (2003) *J Virol* 77:3091-8; Uchil & Satchidanandam (2001) *Am J Trop Med Hyg* 65:242-51). The wide geographical distribution and the existence of multiple strains, coupled with the high rate of mortality and residual neurological complications in survivors, make JEV infection an important public health problem.

The JE-VAX® vaccine currently available in most countries is an inactivated whole virus vaccine prepared from virus grown in mouse brain and a three-dose regimen is required for young children (Monath (2002) *Curr Top Microbiol Immunol* 267:105-38). The requirements of multiple doses and the high vaccine manufacturing cost have prevented many countries from adopting an effective JEV vaccination campaign. A live attenuated vaccine, JEV strain SA14-14-2, has been developed in China and was efficacious after one dose in a recent case-controlled study (Tandan, et al. (2007) *Vaccine* 25:5041-5). In addition, there is a chimeric JEV vaccine constructed from the attenuated yellow fever 17D strain in a late experimental stage (Monath, et al. (2003) *J Infect Dis* 188:1213-30). However, until a JEV vaccine becomes generally available, a need remains for short-term prevention and therapeutic intervention of encephalitic JEV infections.

SUMMARY

Provided herein are isolated humanized monoclonal antibodies that specifically bind and/or neutralize Japanese encephalitis virus (JEV) envelope protein. The humanized monoclonal antibodies bind JEV with an affinity constant ($K_d$) of about 1.0 nM or less. Also provided are isolated humanized monoclonal antibodies that specifically bind to $Lys_{179}$ within a β-strand in domain I of the envelope protein, isolated humanized monoclonal antibodies that specifically bind $Ile_{126}$ within the small loop between d and e β-strands in domain II of the envelope protein, and isolated humanized monoclonal antibodies that specifically bind $Gly_{302}$ within amino acids 302-309 of domain III of the envelope protein. In some embodiments, the human monoclonal antibodies include Fab fragments that include chimpanzee FRs and CDRs. Further provided are compositions including the JEV-specific antibodies, nucleic acids encoding these antibodies, expression vectors including the nucleic acids, and isolated host cells that express the nucleic acids.

Also provided are pharmaceutical compositions that include the humanized JEV-specific monoclonal antibodies.

The antibodies and compositions provided herein can be used for a variety of purposes, such as for treating or inhibiting the development of JEV infection in a subject. Thus, disclosed herein is a method of treating a subject diagnosed with JEV infection or at risk for developing JEV infection, the method including administering to the subject a therapeutically effective amount of the humanized JEV antibody, thereby treating the subject.

The antibodies and compositions provided herein also can be used for diagnosing or confirming the diagnosis of JEV infection in a subject. Thus, provided herein is a method of confirming the diagnosis of JEV infection in a subject, the method including contacting a sample from the subject diagnosed with JEV infection with a human monoclonal antibody that specifically binds JEV, and detecting binding of the antibody to the sample. An increase in binding of the antibody to the sample relative to binding of the antibody to a control sample confirms the JEV infection diagnosis. In some embodiments, the method further includes contacting a second antibody that specifically recognizes the JEV-specific antibody with the sample, and detecting binding of the second antibody.

Similarly, a method is provided herein for detecting JEV infection in a subject, including contacting a sample from the subject with a humanized monoclonal antibody described herein, and detecting binding of the antibody to the sample. An increase in binding of the antibody to the sample relative to a control sample detects JEV infection in the subject. In some embodiments, the methods further include contacting a second antibody that specifically recognizes the JEV-specific antibody with the sample, and detecting binding of the second antibody.

The foregoing and other features and advantages will become more apparent from the following detailed description of several embodiments, which proceeds with reference to the accompanying figures.

BIOLOGICAL DEPOSIT

Plasmids encoding the humanized antibodies A3, B2, and E3 were deposited in accordance with the Budapest Treaty with the American Type Culture Collection (ATCC) Patent Depository, 10801 University Blvd., Manassas, Va., 20110, on Apr. 7, 2008. The plasmid encoding the humanized antibody A3 was deposited as ATCC No. PTA-9138. The plasmid encoding the humanized antibody B2 was deposited as ATCC No. PTA-9139 and the plasmid encoding the humanized antibody E3 was deposited as ATCC No. PTA-9140.

BRIEF DESCRIPTION OF THE FIGURES

FIG. 1 is a diagram showing the alignment of $V_H$ and $V_L$ sequences of chimpanzee JEV-specific Fabs (SEQ ID NOS: 1-6). Fabs were grouped according to the panning strategy: Group 1 (panning with JEV SA14-14-2 virions); Group 2 (panning with epitope masking); and Group 3 (panning with a JEV E domain III-specific recombinant protein). Sequences of the most potently neutralizing Fab in each group are provided ($V_H$ upper panel and $V_L$ lower panel). Framework regions (FR), complementarity determining regions (CDR), sequences identities (.) and deletions (–) are indicated.

In FIG. 3A, purified MAbs were incubated with nitrocellulose membranes blotted with JEV SA14-14-2 strain (upper panel) or the recombinant JEV E protein (lower panel), separated by 4 to 12% SDS-PAGE under non-reducing conditions. HMAF against JEV was included as a positive control. In FIG. 3B, immunoprecipitation of JEV infected mosquito cell lysates (upper panel) or a recombinant JEV E protein (lower panel) was analyzed under non-reducing conditions by Western blotting with MAb 6B4A-10 and anti-mouse IgG-HRP (upper panel) or with MAb anti-V5 epitope-HRP (lower panel). Molecular size markers are shown on the left.

In FIG. 4A, binding in response to different concentrations of purified Fabs was analyzed by ELISA on JEV SA14-14-2 virions attached to the solid phase with HMAF. The Fab concentration required to reach 50% saturation binding was calculated by nonlinear regression. FIG. 4B shows representative sensograms of Fabs A3 (top panel) and B2 (bottom panel) analyzed by SPR with the recombinant JEV E protein, showing curves fitted using a model for continuous ligand distributions, combined with a 2-compartment approximation of mass transport. Experimental data and fitted curves are shown.

FIGS. 5A-5C are a series of graphs showing neutralization of parental JEV and its variants using chimpanzee JEV Fabs. JEV neutralization-escape variants v1, v2 and v3 were selected with the Fabs A3, B2, and E3, respectively. Neutralization titrations by PRNT against parental JEV and antigenic variants v1, v2 and v3 with Fabs A3 (FIG. 5A), B2 (FIG. 5B), and E3 (FIG. 5C) are shown. PRNT was performed using approximately 70 FFU of each virus for incubation with serially diluted antibody at 37° C. for 1 hour. The reaction mixture was used to infect Vero Cells. Foci of infected cells were detected by immuno-staining.

FIGS. 6A-6B is an alignment and 3-D structure model showing the localization of epitope determinants of JEV MAbs. FIG. 6A shows the alignment of amino acid sequences among flavivirus E's. Sequences surrounding the amino acid substitutions found in JEV variants v1, v2 and v3 are shown. Clustal W v2 was used to obtain an optimal amino acid sequence alignment file. SEQ ID NO: 10 is shown. Substitutions are in reference to SEQ ID NO: 10. FIG. 6B shows the 3-D structure model of JEV SA14-14-2 E protein. The structure modeling was performed with the crystal coordinates of WNV (PDB code, 2169) and a Swiss Modeling Workstation. Molecular graphics images were produced using the UCSF Chimera program. Positions of 126Ile, 136Lys, 179Lys, 219His and 302Gly as viewed from the top (upper panel) and from the side (lower panel). E domain sequences are provided in grayscale: domain I includes 136Lys and 179Lys (dark font), domain II includes 126Ile and 219His (light font) and domain III includes 302Gly (dark font).

FIG. 7A shows the binding of humanized MAbs A3, E3 (top panel), and the control mouse MAb anti-V5 epitope (bottom panel) to various mutant proteins as analyzed by Western blotting. The wild type (WT) and mutant E proteins reacted with the indicated antibody and developed with an HRP-conjugated secondary antibody. FIG. 7B shows the binding of MAbs A3, B2 and E3 to WT and mutant E proteins (top panel) and the control mouse MAb 6B4A-10 (bottom panel) analyzed by immunoprecipitation in the absence of detergents. The immunoprecipitates were developed by Western blotting using MAb anti-V5 epitope HRP-conjugate.

SEQUENCE LISTING

Figure 2A:
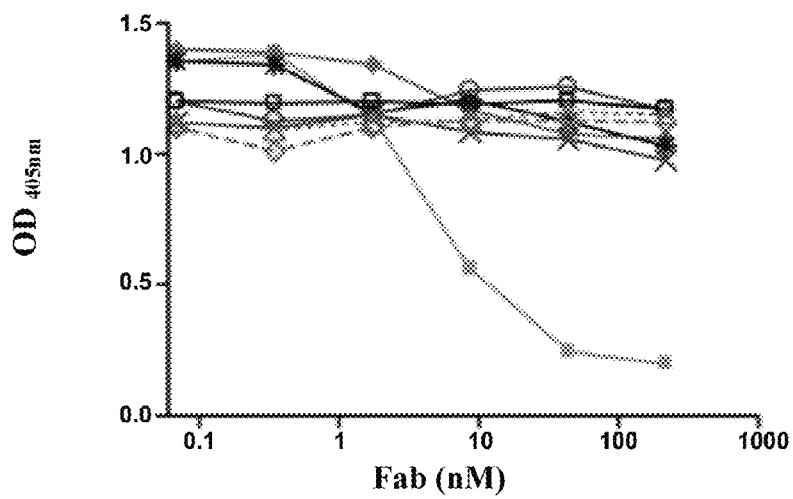
FIGS. 2A-2C are a series of three graphs showing an analysis of Fab binding to JEV SA14-14-2. Fabs A3 (FIG. 2A), B2 (FIG. 2B) and E3 (FIG. 2C) were affinity purified, biotinylated, and used for analysis of binding activity to JEV SA14-14-2 by competition ELISA in the presence of competing, unlabeled Fabs. Fab 5H2, which did not react with JEV, was used as a negative control. Fab 1A5 is a flavivirus cross-reactive antibody that binds to determinants in the flavivirus E fusion loop. JEV Fab clones were grouped according to the panning procedure: Group 1: A3; Group 2: B2, A8 and G1; and Group 3: E3 and B12.

The Sequence Listing is submitted as an ASCII text file (4239-80933-05_Sequence_Listing.txt, Jan. 21, 2016, 36.1 KB), which is incorporated by reference herein.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of the heavy chain of monoclonal antibody A3.

SEQ ID NO: 2 is the amino acid sequence of the heavy chain of monoclonal antibody B2.

SEQ ID NO: 3 is the amino acid sequence of the heavy chain of monoclonal antibody E3.

SEQ ID NO: 4 is the amino acid sequence of the light chain of monoclonal antibody A3.

SEQ ID NO: 5. is the amino acid sequence of the light chain of monoclonal antibody B2.

SEQ ID NO: 6 is the amino acid sequence of the light chain of monoclonal antibody E3.

SEQ ID NO: 7 is the nucleic acid sequence of a forward primer used to amplify the DNA encoding amino acids 131-692 of the PrM/N-terminal 80% E fusion protein from JEV cDNA.

SEQ ID NO: 8 is the nucleic acid sequence of a reverse primer used to amplify the DNA encoding amino acids 131-692 of the PrM/N-terminal 80% E fusion protein from JEV cDNA.

SEQ ID NO: 9 is the nucleic acid sequence encoding JEV ENV protein.

SEQ ID NO: 10 is the amino acid sequence of the JEV ENV protein from JEV strain SA14-14-2.

SEQ ID NO: 11 is the amino acid sequence of the Fc Region of human IgG.

SEQ ID NOs: 12-30 are the amino acid sequences of a deletion at the N-terminal region of the $C_H2$ domain in the Fc region of human IgG.

SEQ ID NO: 31 is the full-length variable region amino acid sequence of the heavy chain of monoclonal antibody A3.

SEQ ID NO: 32 is the full-length variable region amino acid sequence of the heavy chain of monoclonal antibody B2.

SEQ ID NO: 33 is the full-length variable region amino acid sequence of the heavy chain of monoclonal antibody E3.

SEQ ID NO: 34 is the full-length variable region amino acid sequence of the light chain of monoclonal antibody A3.

SEQ ID NO: 35 is the full-length variable region amino acid sequence of the light chain of monoclonal antibody B2.

SEQ ID NO: 36 is the full-length variable region amino acid sequence of the light chain of monoclonal antibody E3.

DETAILED DESCRIPTION

I. Abbreviations

3SR: Self-sustained sequence replication
ADCC: Antibody-dependent cell-mediated cytotoxicity
AST: average survival time
BSA: bovine serum albumin
BRET: bioluminescence resonance energy transfer
C capsid
CDR: Complementarity determining region
DENY: dengue virus
DMEM: Dulbecco's Modified Essential Medium
DTE: dithioerythritol
E: envelope
ELISA: Enzyme-linked immunosorbent assay
EM: Effector molecule
FACS: Fluorescence-activated cell sorting
FBS: Fetal bovine serum
FFU: focus forming units
FITC: Fluorescein isothiocyanate
FRET: fluorescence resonance energy transfer
GFP: Green fluorescent protein
GPI: Glycosylphosphatidylinositol
HMAF: Hyperimmune mouse ascites fluid
HRP: Horseradish peroxidase
I.C.: Intracerebral
Ig: Immunoglobulin
I.P.: intraperitoneal
JEV: Japanese encephalitis virus
LCR: Ligase chain reaction
LDH: Lactate dehydrogenase
LGTV: Langat virus
mAb: Monoclonal antibody
MEM: Minimum Essential Medium
MOI: multiple of infection
MPBS: Milk/PBS
PAGE: Polyacrylamide gel electrophoresis
PBMC: Peripheral blood mononuclear cells
PBS: Phosphate-buffered saline
PBST: PBS-Tween 20
PCR: Polymerase chain reaction
prM/M: pre-membrane/membrane
PRNT: plaque reduction neutralization tests
PE: *Pseudomonas* exotoxin
PEG: Polyethylene glycol
RIA: Radioimmunoassay
S2: Schneider's *Drosophila* Line 2
SDS: Sodium dodecyl sulfate
SLEV: St. Louis encephalitis virus
SC: subcutaneous
SPR: surface plasmon resonance
TAS: transcription-based amplification
WNV: West Nile encephalitis virus
YFP: Yellow fluorescent protein II. Abbreviations, Terms and Methods Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand including at least a light chain or heavy chain immunoglobulin variable region which specifically recognizes and binds an epitope of an antigen, such as JEV envelope protein or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine or humanized chimpanzee antibodies), heteroconjugate antibodies (such as, bispecific antibodies). See also, *Pierce Catalog and Handbook*, 1994-1995 (Pierce Chemical Co., Rockford, Ill.); Kuby, *J., Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds JEV will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a chimpanzee antibody that specifically binds JEV and/or JEV envelope protein.

A "humanized" immunoglobulin is an immunoglobulin including a human framework region and one or more CDRs (or SDRs) from a non-human (for example a mouse, rat, chimpanzee or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, for instance, at least about 85-90%, such as about 95% or more identical. Hence, all parts of a humanized immunoglobulin, except possibly the CDRs, are substantially identical to corresponding parts of natural human immunoglobulin sequences.

A "humanized antibody" is an antibody comprising a humanized light chain and a humanized heavy chain immunoglobulin. A humanized antibody binds to the same antigen as the donor antibody that provides the CDRs. "Humanized" forms of non-human (for instance, murine or chimpanzee) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate, such as chimpanzee, having the desired specificity, affinity, and capacity. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. In general, the humanized antibody will include substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will include at least a portion of an immunoglobulin constant region (Fc), typically that of a human immunoglobulin. In some embodiments, the $C_H2$ and/or $C_H3$ domain is deleted or altered in the Fc region. Humanized immunoglobulins can be constructed by means of genetic engineering (see for example, U.S. Pat. No. 5,585,089).

In one example, the framework and the CDRs are from the same originating human heavy and/or light chain amino acid sequence. However, frameworks from one human antibody can be engineered to include CDRs from a different human antibody.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In one embodiment, the antibodies bind JEV with an affinity constant ($K_d$) of about 1.0 nM or less. In several embodiments, the humanized monoclonal antibodies bind JEV with a binding affinity of about 0.95 nM or less, about 0.85 nM or less, about 0.75 nM or less, about 0.65 nM or less, about 0.55 nM or less, about 0.45 nM or less, about 0.35 nM or less, about 0.25 nM or less, or about 0.15 nM or less. As used herein, a binding affinity of "about 1.0 nM" includes binding affinities of 0.9 to 1.1 nM. Similarly, a binding affinity of "about 0.5 nM" includes binding affinities of 0.4 to 0.6 nM.

Binding domain: The region of a polypeptide that binds to another molecule. In the case of an FcR, the binding domain can include a portion of a polypeptide chain thereof (for instance, the α chain thereof) that is responsible for binding an Fc region. One useful binding domain is the extracellular domain of an FcR α chain.

$C_H2$ domain: The "$C_H2$ domain" of a human IgG Fc region (also referred to as "$C\gamma2$" domain) usually extends from about amino acid 231 to about amino acid 340. The $C_H2$ domain is unique in that it is not closely paired with another domain. Rather, two N-linked branched carbohydrate chains are interposed between the two $C_H2$ domains of an intact native IgG molecule. It has been speculated that the carbohydrate can provide a substitute for the domain—domain pairing and help stabilize the $C_H2$ domain.

$C_H3$ domain: The "$C_H3$ domain" includes the stretch of residues C-terminal to a $C_H2$ domain in an Fc region (for instance, from about amino acid residue 341 to about amino acid residue 447 of an IgG). See, for instance, SEQ ID NO: 11.

Chimeric antibody: An antibody that includes sequences derived from two different antibodies, which typically are of different species. Chimeric antibodies can include human and murine antibody domains, generally human constant regions and murine variable regions, murine CDRs and/or murine SDRs. In other examples, chimeric antibodies include human and chimpanzee antibody domains, generally human constant regions and chimpanzee variable regions, chimpanzee CDRs and/or chimpanzee SDRs.

Conservative variants: "Conservative" amino acid substitutions are those substitutions that do not substantially affect or decrease the affinity of an antibody to JEV. For example, a human antibody that specifically binds JEV can include at most about 1, at most about 2, at most about 5, and most about 10, or at most about 15 conservative substitutions and specifically bind the original JEV polypeptide. The term conservative variation also includes the use of a substituted amino acid in place of an unsubstituted parent amino acid, provided that antibody specifically binds JEV. Non-conservative substitutions are those that reduce an activity or binding to JEV or JEV envelope protein.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Degenerate variant: A polynucleotide encoding a JEV polypeptide or an antibody that binds JEV that includes a sequence that is degenerate as a result of the genetic code. There are 20 natural amino acids, most of which are specified by more than one codon. Therefore, all degenerate nucleotide sequences are included as long as the amino acid sequence of the JEV polypeptide or antibody that binds JEV encoded by the nucleotide sequence is unchanged.

Epitope: An antigenic determinant. These are particular chemical groups or peptide sequences on a molecule that are antigenic, for instance, that elicit a specific immune response. An antibody specifically binds a particular antigenic epitope on a polypeptide, such as JEV envelope protein.

Envelope protein: A membrane that coats the capsid layer of a virus. A capsid is the protein shell of a virus. It includes of several oligomeric subunits made of protein. The capsid encloses the genetic material of the virus.

Capsids are broadly classified according to their structure. The majority of viruses have capsids with either helical or icosahedral structure. Some viruses, such as bacteriophages, have developed more complicated structures. The icosahedral shape, which has 20 equilateral triangular faces, approximates a sphere, while the helical shape is cylindrical. The capsid faces may consist of one or more proteins. For example, the foot-and-mouth disease virus capsid has faces consisting of three proteins named VP1-3.

Some viruses are enveloped, meaning that the capsid is coated with a lipid membrane known as the viral envelope. The envelope is acquired by the capsid from an intracellular membrane in the virus' host; examples of such intracellular membranes include the inner nuclear membrane, the golgi membrane, and the cell's outer membrane.

Expressed: Translation of a nucleic acid into a protein. Proteins can be expressed and remain intracellular, become a component of the cell surface membrane, or be secreted into the extracellular matrix or medium.

Fc region: The term "Fc region" includes a C-terminal region of an immunoglobulin heavy chain. The "Fc region" can be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally includes two constant domains, $C_H2$ and $C_H3$.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity; phagocytosis; down regulation of cell surface receptors (for instance, B cell receptor), etc. Such effector functions generally require the Fc region to be combined with a binding domain (for instance, an antibody variable domain) and can be assessed using various assays as herein disclosed, for example.

A "native sequence Fc region" includes an amino acid sequence identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. In one specific, non-limiting example, a human Fc region amino acid sequence is

```
                                              (SEQ ID NO: 11)
ASTKGPSVFPLAPSSKSTSGGTAALGCLVKDYFPEPVTVSWNSGALTSGV

HTFPAVLQSSGLYSLSSVVTVPSSSLGTQTYICNVDHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

A "variant Fc region" includes an amino acid sequence that differs from that of a native sequence Fc region by virtue of at least one "amino acid modification" as herein defined. Generally, the variant Fc region has at least one amino acid modification compared to a native sequence Fc region or to the Fc region of a parent polypeptide, for instance, from about one to about ten amino acid modifications in a native sequence Fc region or in the Fc region of the parent polypeptide. Embodiments disclosed herein include variant Fc regions that can have the following degrees of amino acid sequence homology or identity to the Fc region of a parent polypeptide, for example: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate variant Fc regions having greater than or equal to a 35% homology or identity can be identified by methods known in the art and can be subsequently examined using functional assays, for example, the assays described herein and those known in the art. The variant Fc regions described herein, in some examples, possess at least about 80% homology with a native sequence Fc region and/or with an Fc region of a parent polypeptide, and most preferably at least about 90% homology therewith, more preferably at least about 95% homology therewith.

The term "Fc region-containing polypeptide" refers to a polypeptide, such as an antibody, that includes an Fc region.

The terms "Fc receptor" or "FcR" are used to describe a receptor that binds to the Fc region of an antibody. In one example, an FcR is a native sequence human FcR. In other examples, an FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif in its cytoplasmic domain. Inhibiting receptor FcγRIIB contains an immunoreceptor tyrosine-based inhibition motif in its cytoplasmic domain. Other FcRs, including those to be identified in the future, are encompassed by the term "FcR" as used herein. The term also includes the neonatal receptor, FcRn, which is responsible for the transfer of maternal IgGs to the fetus. The term includes allotypes, such as FcγRIIIA allotypes: FcγRIIIA-Phe$_{158}$, FcγRIIIA-Val$_{158}$, FcγRIIA-R$_{131}$ and/or FcγRIIA-H$_{131}$.

"Human effector cells" are leukocytes that express one or more FcRs and perform effector functions.

A polypeptide variant with "altered" FcR binding affinity is one that has diminished FcR binding activity compared to a parent polypeptide or to a polypeptide including a native sequence Fc region. The polypeptide variant that "displays decreased binding" to an FcR binds at least one FcR with worse affinity than a parent polypeptide. The decrease in binding compared to a parent polypeptide can be about 40% or more decrease in binding, for instance, down to a variant that possesses little or no appreciable binding to the FcR. Such variants that display decreased binding to an FcR can possess little or no appreciable binding to an FcR, for instance, 0-20% binding to the FcR compared to a native sequence IgG Fc region.

Framework region: Amino acid sequences interposed between CDRs. Framework regions include variable light and variable heavy framework regions. The framework regions serve to hold the CDRs in an appropriate orientation for antigen binding.

Hinge region: A region stretching from Glu216 to Pro230 of human IgG1. Hinge regions of other IgG isotypes can be aligned with the IgG1 sequence by placing the first and last cysteine residues forming inter-heavy chain S—S bonds in the same positions. These regions are well known in the art.

Host cells: Cells in which a vector can be propagated and its DNA expressed. The cell can be prokaryotic or eukaryotic. The term also includes any progeny of the subject host cell. It is understood that all progeny may not be identical to the parental cell since there can be mutations that occur during replication. However, such progeny are included when the term "host cell" is used.

Hypervariable region: The amino acid residues of an antibody that are responsible for antigen-binding. The hypervariable region includes amino acid residues from a "complementarity determining region" or "CDR" (for instance, residues 24-34 (L1), 50-56 (L2) and 89-97 (L3) in the light chain variable domain and 31-35 (H1), 50-65 (H2) and 95-102 (H3) in the heavy chain variable domain and/or those residues from a "hypervariable loop" (for instance, residues 26-32 (L1), 50-52 (L2) and 91-96 (L3) in the light chain variable domain and 26-32 (H1), 53-55 (H2) and 96-101 (H3) in the heavy chain variable domain. "Framework" or "FR" residues are those variable domain residues other than the hypervariable region residues as herein defined.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic peptide: A peptide such as an envelope protein which includes an allele-specific motif or other sequence, such as an N-terminal repeat, such that the peptide will bind an MHC molecule and induce a cytotoxic T lymphocyte ("CTL") response, or a B cell response (for example, antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure can provide a contact point with the immunogenic peptide. In one specific non-limiting example, an immunogenic polypeptide includes a region of JEV envelope protein, or a fragment thereof.

Immunogenic composition: A composition including a JEV polypeptide, such as an envelope protein that induces a measurable CTL response against cells expressing JEV polypeptide, or induces a measurable B cell response (such as production of antibodies) against a JEV polypeptide. It further refers to isolated nucleic acids encoding a JEV polypeptide that can be used to express the JEV polypeptide (and thus be used to elicit an immune response against this polypeptide). For in vitro use, an immunogenic composition can consist of the isolated protein or peptide epitope. For in vivo use, the immunogenic composition will typically include the protein or immunogenic peptide in pharmaceutically acceptable carriers, and/or other agents. Any particular peptide, such as a JEV polypeptide, or nucleic acid encoding the polypeptide, can be readily tested for its ability to induce a CTL or B cell response by art-recognized assays Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, and pH) that are typical inside a living mammal or a mammalian cell. While it is recognized that some organs are subject to extreme conditions, the intra-organismal and intracellular environment normally lies around pH 7 (for instance, from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component, such as a nucleic acid, protein (including antibodies) or organelle, has been substantially separated or purified away from other biological components in the environment (such as a cell) in which the component naturally occurs, for instance, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Japanese encephalitis virus (JEV): The virus that causes the mosquito-borne disease Japanese encephalitis. JEV is a virus from the family Flaviviridae. Domestic pigs and wild birds are reservoirs of the virus; transmission to humans may cause severe symptoms. One of the most important vectors of this disease is the mosquito *Culex tritaeniorhynchus*. This disease is most prevalent in Southeast Asia and the Far East.

JEV is an enveloped virus of the genus flavivirus; it is closely related to the West Nile virus and St. Louis encephalitis virus. Positive sense single stranded RNA genome is packaged in the capsid, formed by the capsid protein. The outer envelope is formed by envelope (E) protein and is the protective antigen. The genome also encodes several nonstructural proteins (NS1, NS2a, NS2b, NS3, N4a, NS4b, NS5). NS1 is produced as secretory form also. NS3 is a putative helicase, and NS5 is the viral polymerase. It has been noted that the Japanese encephalitis virus (JEV) infects the lumen of the endoplasmic reticulum and rapidly accumulates substantial amounts of viral proteins for the JEV.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and can be used. Examples of labels for polypeptides include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule, such as a label. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Major histocompatibility complex (MHC): Generic designation meant to encompass the histocompatibility antigen systems described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for instance, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

"Recombinant nucleic acid" refers to a nucleic acid having nucleotide sequences that are not naturally joined together. This includes nucleic acid vectors including an amplified or assembled nucleic acid which can be used to transform a suitable host cell. A host cell that includes the recombinant nucleic acid is referred to as a "recombinant host cell." The gene is then expressed in the recombinant host cell to produce, such as a "recombinant polypeptide." A recombinant nucleic acid can serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; and Corpet et al., *Nucleic Acids Research* 16:10881, 1988.

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Passive immunization: A type of immunization in which pre-made elements of the immune system (for instance, antibodies) are transferred to a subject. Passive immunization occurs naturally during the transfer of antibodies from mother to fetus during pregnancy. Artificial passive immunization is normally administered parenterally, and is particularly effective as both a therapeutic and a preventative strategy during an outbreak of a particular disease or as an emergency treatment to toxins (for example, for tetanus). Passive immunization also is used when there is a high risk of infection and insufficient time for the body to develop its own immune response, or to reduce the symptoms of ongoing or immunosuppressive diseases.

Artificially acquired passive immunity is a short-term immunization achieved by the transfer of antibodies, which can be administered in several forms; as human or animal blood plasma or serum, as pooled human immunoglobulin for intravenous (IVIG) or intramuscular (IG) use, as high-titer human IVIG or IG from immunized or from donors recovering from the disease, and as monoclonal antibodies (MAb). Passive transfer is used prophylactically in the case of immunodeficiency diseases, such as hypogammaglobulinemia. It is also used in the treatment of several types of acute infection, and to treat poisoning Immunity derived from passive immunization lasts for only a short period of time, and there is also a potential risk for hypersensitivity reactions, and serum sickness, especially from gamma globulin of non-human origin. Passive immunity provides immediate protection, but the body does not develop memory, therefore the patient is at risk of being infected by the same pathogen later. Methods of passive immunization are discussed in greater detail below in the Detailed Description.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). In one embodiment, the polypeptide is JEV envelope polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease, such as JEV infection.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

The JEV polypeptides disclosed herein, or antibodies that specifically bind JEV or a JEV polypeptide such as a envelope polypeptide, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement).

Another example of algorithms that are suitable for determining percent sequence identity and sequence similarity are the National Center for Biotechnology Information (NCBI) Basic Local Alignment Search Tool (BLAST) and the BLAST 2.0 algorithm, which are described in Altschul et al., *J. Mol. Biol.* 215:403-410, 1990 and Altschul et al., *Nucleic Acids Res.* 25:3389-3402, 1997. The BLAST tool is available from several sources, including the National Center for Biotechnology Information (NCBI, Bethesda, Md.) and on the internet (http://www.ncbi.nlm.nih.gov/), for use in connection with the sequence analysis programs such as BLASTP, BLASTN, BLASTX, TBLASTN and TBLASTX. For example, the BLASTN program (for nucleotide sequences) uses as defaults a word length (W) of 11, alignments (B) of 50, expectation (E) of 10, M=5, N=−4, and a comparison of both strands. In another example, the BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). A description of how to determine sequence identity using this program is available on the NCBI website on the internet.

Homologs and variants of a $V_L$ or a $V_H$ of an antibody that specifically binds JEV or a JEV envelope polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus, a JEV specific binding agent is an agent that binds substantially to a JEV polypeptide. In one embodiment, the specific binding agent is a humanized monoclonal antibody that specifically binds the JEV polypeptide.

The term "specifically binds" refers, with respect to an antigen such as JEV envelope protein, to the preferential association of an antibody or other ligand, in whole or part, with a cell or tissue bearing that antigen and not to cells or tissues lacking that antigen. It is recognized that a certain degree of non-specific interaction can occur between a molecule and a non-target cell or tissue. Nevertheless, specific binding can be distinguished as mediated through specific recognition of the antigen. Although selectively reactive antibodies bind antigen, they can do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the JEV polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress the development of an infection, or to substantially reduce the symptoms of an infection, for instance a JEV infection. In one embodiment, a therapeutically effective amount is the amount necessary to eliminate a JEV infection. When administered to a subject, a dosage will generally be used that will achieve target tissue concentrations that has been shown to achieve a desired in vitro effect.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Treatment: Refers to both therapeutic treatment and prophylactic or preventative measures. Those in need of treatment include those already with the disorder as well as those in which the disorder is to be prevented.

Vector: A nucleic acid molecule as introduced into a host cell, thereby producing a transformed host cell. A vector can include nucleic acid sequences that permit it to replicate in a host cell, such as an origin of replication. A vector can also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Humanized Monoclonal Antibodies that Specifically Bind JEV

Described herein are isolated humanized monoclonal antibodies that specifically bind Japanese encephalitis virus (JEV). The humanized monoclonal antibodies bind JEV with an affinity constant ($K_d$) of about 1.0 nM or less. In some embodiments, the $K_d$ is about 0.98 nM, about 0.95 nM or less, about 0.90 nM or less, about 0.85 nM or less, about 0.80 nM or less, about 0.75 nM or less, about 0.72 nM or less, about 0.70 nM or less, about 0.65 nM or less, about 0.60 nM or less, or about 0.55 nM or less. In other embodiments, the $K_d$ is about 0.50 nM or less, about 0.45 nM or less, about 0.40 nM or less, about 0.35 nM or less, about 0.30 nM or less, about 0.28 nM or less, about 0.25 nM, about 0.20 nM, about 0.15 nM or about 0.05 nM or less. As used herein, a binding affinity of "about 0.05 nM" includes binding affinities of 0.04 nM to 0.06 nM. Similarly, a binding affinity of "about 0.15 nM" includes binding affinities of 0.1 nM to 0.2 nM.

In some embodiments, the humanized monoclonal antibodies specifically bind JEV envelope protein (ENV). In one embodiment, the human monoclonal antibodies bind the JEV envelope protein of JEV strain SA14-14-2 (GenBank Accession No: AF315119). In one non-limiting example, the nucleic acid sequence encoding JEV ENV is (SEQ ID NO: 9)
TTTAATTGTCTGGGAATGGGCAATCGTGACTTCATAGAAGGAGCCAGTG

GAGCCACTTGGGTGGACTTGGTGCTAGAAGGAGACAGCTGCTTGACAAT

CATGGCAAACGACAAACCAACATTGGACGTCCGCATGATTAACATCGAA

GCTAGCCAACTTGCTGAGGTCAGAAGTTACTGCTATCATGCTTCAGTCAC

TGACATCTCGACGGTGGCTCGGTGCCCCACGACTGGAGAAGCCCACAAC

GAGAAGCGAGCTGATAGTAGCTATGTGTGCAAACAAGGCTTCACTGACC

GTGGGTGGGGCAACGGATGTGGATTTTTCGGGAAGGGAAGCATTGACAC

ATGTGCAAAATTCTCCTGCACCAGTAAAGCGATTGGGAGAACAATCCAG

CCAGAAAACATCAAATACAAAGTTGGCATTTTTGTGCATGGAACCACCA

CTTCGGAAAACCATGGGAATTATTCAGCGCAAGTTGGGGCGTCCCAGGC

GGCAAAGTTTACAGTAACACCCAATGCTCCTTCGGTAGCCCTCAAACTTG

GTGACTACGGAGAAGTCACACTGGACTGTGAGCCAAGGAGTGGACTGAA

CACTGAAGCGTTTTACGTCATGACCGTGGGGTCAAAGTCATTTCTGGTCC

ATAGGGAGTGGTTTCATGACCTCGCTCTCCCCTGGACGTCCCCTTCGAGC

ACAGCGTGGAGAAACAGAGAACTCCTCATGGAATTTGAAGGGCGCAC

GCCACAAAACAGTCCGTTGTTGCTCTTGGGTCACAGGAAGGAGGCCTCC

ATCATGCGTTGGCAGGAGCCATCGTGGTGGAGTACTCAAGCTCAGTGAT

GTTAACATCAGGCCACCTGAAATGTAGGCTGAAAATGGACAAACTGGCT

CTGAAAGGCACAACCTATGGCATGTGTACAGAAAAATTCTCGTTCGCGA

AAAATCCGGTGGACACTGGTCACGGAACAGTTGTCATTGAACTCTCCTA

CTCTGGGAGTGATGGCCCCTGCAAAATTCCGATTGTTTCCGTTGCGAGCC

TCAATGACATGACCCCCGTTGGGCGGCTGGTGACAGTGAACCCCTTCGTC

GCGACTTCCAGTGCCAACTCAAAGGTGCTGGTCGAGATGGAACCCCCCT

TCGGAGACTCCTACATCGTAGTTGGAAGGGGAGACAAGCAGATCAACCA

CCATTGGCACAAAGCTGGAAGCACGCTGGGCAAGGCCTTTTCAACAACT

TTGAAGGGAGCTCAAAGACTGGCAGCGTTGGGCGACACAGCCTGGGACT

TTGGCTCTATTGGAGGGGTCTTCAACTCCATAGGAAGAGCCGTTCACCAA

GTGTTTGGTGATGCCTTCAGAACACTCTTTGGGGAATGTCTTGGATCAC

ACAAGGGCTAATGGGTGCCCTACTGCTCTGGATGGGCGTCAACGCACGA

GACCGATCAATTGCTTTGGCCTTCTTAGCCACAGGAGGTGTGCTCGTGTT

CTTAGCGACCAATGTGCATGCT.

In another non-limiting example, the amino acid sequence of the JEV envelope protein is (SEQ ID NO: 10)
FNCLGMGNRDFIEGASGATWVDLVLEGDSCLTIMANDKPTLDVRMINIEA

SQLAEVRSYCYHASVTDISTVARCPTTGEAHNEKRADSSYVCKQGFTDRG

WGNGCGFFGKGSIDTCAKFSCTSKAIGRTIQPENIKYKVGIFVHGTTTSE

NHGNYSAQVGASQAAKFTVTPNAPSVALKLGDYGEVTLDCEPRSGLNTEA

-continued

```
FYVMTVGSKSFLVHREWFHDLALPWTSPSSTAWRNRELLMEFEGAHATKQ

SVVALGSQEGGLHHALAGAIVEYSSSVMLTSGHLKCRLKMDKLALKGTTY

GMCTEKFSFAKNPVDTGHGTVVIELSYSGSDGPCKIPIVSVASLNDMTPV

GRLVTVNPFVATSSANSKVLVEMEPPFGDSYIVVGRGDKQINHHWHKAGS

TLGKAFSTTLKGAQRLAALGDTAWDFGSIGGVFNSIGRAVHQVFGDAFRT

LFGGMSWITQGLMGALLLWMGVNARDRSIALAFLATGGVLVFLATNVHA.
```

The envelope protein is the main functional and antigenic surface component of the virion. The molecular structure of the ectodomain of the envelope protein, which forms a homodimer on the surface of mature viral particles at neutral pH, has been resolved by cryoelectron microscopy (Rey et al., Nature 375:291-298, 1995, incorporated by reference herein) and fitted into the electron density map of viral particles (Kuhn et al., Cell 108:717-725, 2002). The polypeptide chain of the envelope protein folds into three distinct domains: a central domain (domain I), a dimerization domain (domain II), and an immunoglobulin-like module domain (domain III). The hinge region is present between domains I and II and, upon exposure to acidic pH, undergoes a conformational change (hence the designation "hinge") that results in the formation of envelope protein trimers that are involved in the fusion of viral and endosomal membranes, after virus uptake by receptor-mediated endocytosis. The humanized monoclonal antibody can specifically bind to $Lys_{179}$ within a β-strand in domain I of the envelope protein. The humanized monoclonal antibody can specifically bind $Ile_{126}$ within the small loop between d and e β-strands in domain II of the envelope protein. The humanized monoclonal antibody can specifically bind $Gly_{302}$ within amino acids 302-309 of domain III of the envelope protein.

In some embodiments, the human monoclonal antibodies include Fab fragments that include chimpanzee CDRs. Further provided are compositions including the JEV-specific antibodies, nucleic acids encoding these antibodies, expression vectors including the nucleic acids, and isolated host cells that express the nucleic acids. Also described are compositions including the provided humanized monoclonal antibodies and a pharmaceutically acceptable carrier. Nucleic acids encoding these antibodies, expression vectors including these nucleic acids, and isolated host cells that express the nucleic acids also are provided.

Compositions including the humanized monoclonal antibodies specific for JEV can be used for diagnostic, research and therapeutic purposes. For example, the humanized monoclonal antibodies can be used to treat a subject diagnosed with JEV infection, or to prevent the development of JEV infection in s subject at risk for contracting JEV. The humanized monoclonal antibodies also can be used to diagnose JEV infection in a subject. For example, the humanized monoclonal antibodies can be contacted with a sample from the patient, such as a blood sample, to detect JEV in the sample. The antibodies and compositions provided herein can also be used to detect JEV in a subject or to confirm the diagnosis of JEV infection in a patient.

Disclosed herein are humanized monoclonal antibodies that specifically bind JEV. A major limitation in the clinical use of animal monoclonal antibodies, for instance, mouse or sheep monoclonal antibodies is the development of an anti-mouse or anti-sheep antibody response in the subjects receiving the treatments. The response can involve allergic reactions and an increased rate of clearance of the administered antibody from the serum. Various types of modified monoclonal antibodies have been developed to minimize the antibody response while trying to maintain the antigen binding affinity of the parent monoclonal antibody. One type of modified monoclonal antibody is a humanized chimera in which an animal (for instance mouse, sheep or chimpanzee) antigen-binding variable region is coupled to a human constant domain (Morrison & Schlom, *Important Advances in Oncology*, Rosenberg, S. A. (Ed.), 1989). A second type of modified monoclonal antibody is the complementarity determining region (CDR)-grafted, or humanized, monoclonal antibody (Winter & Harris, *Immunol. Today* 14:243-246, 1993). Still other monoclonal antibodies of use include non-human primate antibodies, for example chimpanzee or macaque antibodies, for which the amino acid sequences are close enough to human sequences that no anti-chimpanzee or anti-macaque antibodies are generated by the subject receiving the treatment.

In one embodiment, the antibodies bind JEV with an affinity constant ($K_d$) of about 1.0 nM or less. In several embodiments, the human monoclonal antibodies bind JEV with a binding affinity of about 0.98 nM, about 0.72 nM or less, about 0.45 nM or less, about 0.35 nM or less, about 0.28 nM or less, or about 0.15 nM or less.

In other embodiments, the antibody is a chimeric antibody, chimpanzee antibody, or a humanized monoclonal antibody. The antibody can include one or more CDRs of the heavy chain amino acid sequence set forth as SEQ ID NO: 1, SEQ ID NO: 2, or SEQ ID NO: 3. In several embodiments, the heavy chain of the antibody comprises amino acids 31-35 of SEQ ID NO: 1, amino acids 50-66 of SEQ ID NO: 1, and/or amino acids 96-107 of SEQ ID NO: 1. In additional embodiments, the heavy chain of the antibody comprises amino acids 32-36 of SEQ ID NO: 2, amino acids 50-67 of SEQ ID NO: 2, and/or amino acids 100-113 of SEQ ID NO: 2. In further embodiments, the heavy chain of the antibody comprises amino acids 30-37 of SEQ ID NO: 3, amino acids 52-67 of SEQ ID NO: 3 and/or amino acids 100-112 of SEQ ID NO: 3. Thus, in several examples, the heavy chain of the antibody comprises one of (a) amino acids 31-35 of SEQ ID NO: 1, amino acids 50-66 of SEQ ID NO: 1, and amino acids 96-107 of SEQ ID NO: 1; (b) amino acids 32-36 of SEQ ID NO: 2, amino acids 50-67 of SEQ ID NO: 2, and amino acids 100-113 of SEQ ID NO: 2; or (c) amino acids 30-37 of SEQ ID NO: 3, amino acids 52-67 of SEQ ID NO: 3, and amino acids 100-112 of SEQ ID NO: 3. The heavy chain of the antibody can include, or consist of, one of SEQ ID NO: 1, SEQ ID NO: 2, or SEQ ID NO: 3.

In additional embodiments, the antibody can include one or more of the CDRs of the light chain amino acid sequence set forth as SEQ ID NO: 4, SEQ ID NO: 5 or SEQ ID NO: 6. In several embodiments, the light chain of the antibody can include amino acids 24-34 of SEQ ID NO: 4, amino acids 50-56 of SEQ ID NO: 4 and/or amino acids 89-96 of SEQ ID NO: 4. In further embodiments, the light chain of the antibody can include amino acids 24-34 of SEQ ID NO: 5, amino acids 50-56 of SEQ ID NO: 5; or amino acids 89-96 of SEQ ID NO: 5. In other embodiments the light chain of the antibody can include amino acids 22-33 of SEQ ID NO: 6, acids 49-55 of SEQ ID NO 6, and/or amino acids 88-95 of SEQ ID NO: 6.

In several examples, the light chain of the antibody comprises: (a) amino acids 24-34 of SEQ ID NO: 4, amino acids 50-56 of SEQ ID NO: 4, and amino acids 89-96 of SEQ ID NO: 4; (b) amino acids 24-34 of SEQ ID NO: 5 amino acids 50-56 of SEQ ID NO: 5, and amino acids 89-96 of SEQ ID NO: 5; or (c) amino acids 22-33 of SEQ ID NO:

6, amino acids 49-55 of SEQ ID NO: 6, and amino acids 88-95 of SEQ ID NO: 6. The heavy chain of the antibody can include, or consist of, one of SEQ ID NO: 4, SEQ ID NO: 4, or SEQ ID NO: 6.

In one example, the heavy chain of the antibody comprises amino acids 31-35, 50-66 and 96-107 of SEQ ID NO: 1, and the light chain of the antibody comprises amino acids 24-34, 50-56 and 89-96 of SEQ ID NO: 4. In another example, the heavy chain of the antibody comprises amino acids 32-36, 50-67 and 100-113 of SEQ ID NO: 2, and the light chain of the antibody comprises amino acids 24-34, 50-56 and 89-96 of SEQ ID NO: 5. In a further example, the heavy chain of the antibody comprises amino acids 30-37, 52-67 and 100-112 of SEQ ID NO: 3, and the light chain of the antibody comprises amino acids 22-33, 49-55 and 88-95 of SEQ ID NO: 6. In other examples, (a) the heavy chain of the antibody is the amino acid sequence set forth as SEQ ID NO: 1 and the light chain of the antibody is the amino acid sequence set forth as SEQ ID NO: 4; (b) the heavy chain of the antibody is the amino acid sequence set forth as SEQ ID NO: 2 and the light chain of the antibody is the amino acid sequence set forth as SEQ ID NO: 5, or (c) the heavy chain of the antibody is the amino acid sequence set forth as SEQ ID NO: 3 and the light chain of the antibody is the amino acid sequence set forth as SEQ ID NO: 6.

The monoclonal antibody can be of any isotype. The monoclonal antibody can be, for example, an IgM or an IgG antibody, such as $IgG_1$ or an $IgG_2$. The class of an antibody that specifically binds JEV can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that includes a $C_L$ or $C_H$ chain, as known in the art. For example, an antibody that specifically binds JEV that was originally IgM can be class switched to an IgG. Class switching can be used to convert one IgG subclass to another, such as from $IgG_1$ to $IgG_2$.

Humanized monoclonal antibodies include a human framework region. This human framework region can include the framework regions disclosed in SEQ ID NO: 1, SEQ ID NO: 2, SEQ ID NO: 3, SEQ ID NO: 4, SEQ ID NO: 5, or SEQ ID NO: 6 (these sequences include CDR sequences as well as framework sequences). In another embodiment, the human framework region can include the framework regions disclosed in SEQ ID NO:31, SEQ ID NO: 32, SEQ ID NO: 33, SEQ ID NO: 34, SEQ ID NO: 35, or SEQ ID NO: 36. However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16), which is herein incorporated by reference.

Antibody fragments are encompassed by the present disclosure, such as Fab, $F(ab')_2$, and Fv which include a heavy chain and light chain variable region and are capable of binding the epitopic determinant on JEV. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody ($scFV_2$), defined as a dimer of a scFV. This has also been termed a "miniantibody."

Methods of making these fragments are known in the art (see for example, Harlow & Lane, *Antibodies: A Laboratory Manual*, Cold Spring Harbor Laboratory, New York, 1988).

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) are prepared by constructing a structural gene including DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody ($scFV_2$), also are contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques can also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Additional recombinant anti-JEV humanized antibodies can be isolated by screening additional recombinant combinatorial antibody libraries, such as a Fab phage display library (see, for example, U.S. Pre-Grant Publication No. 2005/0123900, incorporated herein by reference). In some cases the phage display libraries are prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., Bio/Technology 9:1370-1372, 1991; Hay et al., Hum. Antibod. Hybridomas 3:81-85, 1992; Huse et al., Science 246:1275-1281, 1989; McCafferty et al., Nature 348:552-554, 1990; Griffiths et al. EMBO J 12:725-734, 1993).

In one embodiment, to isolate additional human antibodies that specifically bind JEV, a human antibody that specifically binds JEV, as described herein, is first used to select human heavy and light chain sequences having similar binding activity toward JEV, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., *Nature* 348:552-554, 1990; and/or Griffiths et al., *EMBO J.* 12:725-734, 1993 using JEV as the antigen.

Once initial human variable light chain ($V_L$) and variable heavy chain ($V_H$) segments are selected, "mix and match" experiments, in which different pairs of the initially selected $V_L$ and $V_H$ segments are screened for JEV binding, are performed to select $V_L/V_H$ pair combinations of interest. Additionally, to increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. This in vitro affinity maturation can be accomplished by amplifying $V_H$ and $V_L$ regions using PCR primers complimentary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for JEV.

Following screening and isolation of an antibody that binds JEV from a recombinant immunoglobulin display library, nucleic acid encoding the selected antibody can be recovered from the display package (for example, from the phage genome) and subcloned into other expression vectors by standard recombinant DNA techniques, as described herein. If desired, the nucleic acid can be further manipulated to create other antibody fragments, also as described herein. To express a recombinant human antibody isolated by screening of a combinatorial library, the DNA encoding the antibody is cloned into a recombinant expression vector and introduced into a mammalian host cells, as described herein.

IV. JEV Antibody Polynucleotides and Polypeptides

Nucleic acid molecules (also referred to as polynucleotides) encoding the polypeptides provided herein (including, but not limited to antibodies) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies, conjugates and fusion proteins are provided herein. In some embodiments, the nucleotide sequence of the heavy chain of the JEV-specific human monoclonal antibody A3 comprises SEQ ID NO: 1, or a portion thereof (such as a portion that encodes one or more CDRs). In some embodiments, the amino acid sequence of the light chain of the JEV-specific human monoclonal antibody A3 comprises SEQ ID NO: 4, or a portion thereof (such as a portion that encodes one or more CDRs).

In one embodiment, the nucleotide sequence of the heavy chain of the JEV-specific human monoclonal antibody B2 comprises SEQ ID NO: 2, or a portion thereof (such as a portion that encodes one or more CDRs). In one embodiment, the amino acid sequence of the light chain of the JEV-specific human monoclonal antibody B2 comprises SEQ ID NO: 5, or a portion thereof (such as a portion that encodes one or more CDRs).

In yet another embodiment, the nucleotide sequence of the heavy chain of the JEV-specific human monoclonal antibody E3 comprises SEQ ID NO: 3, or a portion thereof (such as a portion that encodes one or more CDRs). In another embodiment, the amino acid sequence of the light chain of the JEV-specific human monoclonal antibody E3 comprises SEQ ID NO: 6, or a portion thereof (such as a portion that encodes one or more CDRs).

Nucleic acid sequences encoding the humanized antibodies that specifically bind JEV can be prepared by any suitable method including, for example, cloning of appropriate sequences or by direct chemical synthesis by methods such as the phosphodiester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences can be obtained by the ligation of shorter sequences.

Exemplary nucleic acids encoding humanized antibodies that specifically bind JEV can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding anti-JEV antibodies can be modified to form the antibodies of the present disclosure. Modification by site-directed mutagenesis is well known in the art. Nucleic acids also can be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, antibodies are prepared by inserting the cDNA which encodes a humanized JEV-specific monoclonal antibody into a vector. In one embodiment, cDNA encoding a label or enzyme is ligated to an antibody so that the label or enzyme is located at the carboxyl terminus of the antibody. In another embodiment, the label or enzyme is located at the amino terminus of the antibody. In another example, cDNA encoding the label or enzyme is ligated to a heavy chain variable region of an antibody, so that the label or enzyme is located at the carboxyl terminus of the heavy chain variable region. The heavy chain-variable region can subsequently be ligated to a light chain variable region of the antibody using disulfide bonds. In a yet another example, cDNA encoding a label or enzyme is ligated to a light chain variable region of an antibody, so that the label or enzyme is located at the carboxyl terminus of the light chain variable region. The light chain-variable region can subsequently be ligated to a heavy chain variable region of the antibody using disulfide bonds.

Once the nucleic acids encoding the anti-JEV antibody are isolated and cloned, the desired protein can be expressed in a recombinantly engineered cell such as bacteria, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell can be prokaryotic or eukaryotic. The term also includes any progeny of the subject host cell. It is understood that all progeny can not be identical to the parental cell since there can be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated proteins described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (for instance, ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein (for instance, a humanized JEV-specific monoclonal antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. Modification can also be used to construct an Fc deletion (see below). In addition to recombinant methods, the antibodies of the present disclosure can also be constructed in whole or in part using standard peptide synthesis well known in the art.

Once expressed, the recombinant antibodies can be purified according to standard procedures of the art, including ammonium sulfate precipitation, affinity columns, column chromatography, and the like (see, generally, R. Scopes, *Protein Purification*, Springer-Verlag, N. Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., (1992) *Anal. Biochem.* 205:263-270; Pluckthun, (1991) *Biotechnology* 9:545; Huse et al., (1989) *Science* 246:1275; and Ward et al., (1989) *Nature* 341:544.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione, and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., (1963) *J. Am. Chem. Soc.* 85:2149-2156; and Stewart et al., (1984) *Solid Phase Peptide Synthesis*, 2nd ed., Pierce Chem. Co., Rockford, Ill. Proteins of greater length can be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

V. Fc Deletion Mutants with Reduced Fcγ Receptor Binding Affinity

Also disclosed herein are deletion mutants of the JEV antibodies that have a deletion of about nine amino acids (from about position 231 to about position 239) at the N-terminus of the $C_H2$ domain in the Fc region. By a deletion of "about nine" amino acids are meant a deletion of at least one amino acid from about position 231 to about position 239 at the N-terminus of the $C_H2$ domain in the Fc region. In some embodiments, deletion of "about nine" amino acids refers to a deletion of about 4 amino acids having the sequence LLGG (SEQ ID NO: 12), and no more than 10 amino acids. In another embodiment, a deletion of "about nine" amino acids is meant a deletion of one, two, three, four, five, six, seven, eight, nine or ten amino acids from about position 231 to about position 239 at the N-terminus of the $C_H2$ domain in the Fc region. The Fcγ receptor class I binding site in human IgG has been identified as the sequence spanning residues 234-237 (LLGG; Chappel et al. *Proc Natl Acad Sci USA* 88:9036-9040). For example, such deletions (Table 1) remove the following amino acids:

TABLE 1

Deleted Sequences

| Number of Amino Acids Deleted | Deleted Sequence | SEQ ID NO: |
|---|---|---|
| 4 | LLGG | 12 |
| 5 | ELLGG | 13 |
|   | LLGGP | 14 |
| 6 | PELLGG | 15 |
|   | ELLGGP | 16 |
|   | LLGGPS | 17 |

TABLE 1-continued

Deleted Sequences

| Number of Amino Acids Deleted | Deleted Sequence | SEQ ID NO: |
|---|---|---|
| 7 | APELLGG | 18 |
|   | PELLGGP | 19 |
|   | ELLGGPS | 20 |
|   | LLGGPSV | 21 |
| 8 | PAPELLGG | 22 |
|   | APELLGGP | 23 |
|   | PELLGGPS | 24 |
|   | ELLGGPSV | 25 |
| 9 | PAPELLGGP | 26 |
|   | APELLGGPS | 27 |
|   | PELLGGPSV | 28 |
| 10 | PAPELLGGPS | 29 |
|   | APELLGGPSV | 30 |

The "parent", "starting" or "nonvariant" polypeptide is prepared using techniques available in the art for generating polypeptides including an Fc region. In some embodiments, the parent polypeptide is a humanized monoclonal antibody that specifically binds JEV. A variant Fc region can be generated and this "variant Fc region" then can be fused to a heterologous antibody variable domain of the humanized monoclonal antibody that specifically binds JEV and/or JEV envelope protein.

The parent polypeptide includes an Fc region. Generally the Fc region of the parent polypeptide will include a native sequence Fc region, and preferably a human native sequence Fc region. However, the Fc region of the parent polypeptide can have one or more pre-existing amino acid sequence alterations or modifications from a native sequence Fc region. In a further embodiment the parent polypeptide Fc region is "conceptual" and, while it does not physically exist, the antibody engineer can decide upon a desired variant Fc region amino acid sequence and generate a polypeptide including that sequence or a DNA encoding the desired variant Fc region amino acid sequence. In some embodiments, however, a nucleic acid encoding an Fc region of a parent polypeptide is available and this nucleic acid sequence is altered to generate a variant nucleic acid sequence encoding the Fc region variant.

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Site-directed mutagenesis is a preferred method for preparing substitution variants. This technique is well known in the art (see, for instance, Kunkel et al. 1987 *Proc Natl Acad Sci USA* 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide. See *PCR Protocols: A guide to methods and applications*, Michael A. Innis, chapter by Higuchi, pp. 177-183 (Academic Press, 1990). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al. 1985 *Gene* 34:315-323. The starting material is the plasmid (or other vector) including the starting polypeptide DNA to be mutated. The codon(s) in the starting DNA to be mutated are identified. There must be a unique restriction endonuclease site on each side of the identified mutation site(s). If no such restriction sites exist, they can be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Alternatively, or additionally, the desired amino acid sequence encoding a polypeptide variant can be determined, and a nucleic acid sequence encoding such amino acid sequence variant can be generated synthetically.

The amino acid sequence of the parent polypeptide, specifically the humanized monoclonal antibody that specifically binds JEV is modified in order to generate a variant Fc region with altered Fc receptor binding affinity or activity in vitro and/or in vivo. For example, about nine amino acids (from about position 231 to about position 239) can be deleted at the N-terminus of the $C_H2$ domain in the Fc region. The Fc region herein including one or more amino acid deletions can retain at least about 80%, such as at least about 90%, such as at least about 95%, of the parent Fc region or of a native sequence human Fc region. In some embodiments, the parent polypeptide Fc region is a human Fc region, for instance, a native sequence human Fc region human IgG1 (A and non-A allotypes), IgG2, IgG3 or IgG4 Fc region.

The humanized monoclonal antibodies prepared as described above can be subjected to further modifications, oftentimes depending on the intended use of the polypeptide. Such modifications can involve further alteration of the amino acid sequence (substitution, insertion and/or deletion of amino acid residues), fusion to heterologous polypeptide(s) and/or covalent modifications. Such "further modifications" can be made prior to, simultaneously with, or following, the amino acid modification(s) disclosed above that result in an alteration of Fc receptor binding. In one embodiment, one can combine the Fc region modification herein with another Fc region modification. Alternatively or additionally, it can be useful to combine the above amino acid modifications with one or more further amino acid modifications that alter FcRn binding and/or half-life of the antibody.

With respect to further amino acid sequence alterations, any cysteine residue not involved in maintaining the proper conformation of the humanized antibody also can be substituted, generally with serine, to improve the oxidative stability of the molecule and prevent aberrant cross linking. The humanized monoclonal antibody that specifically binds JEV can be subjected to one or more assays to evaluate any change in biological activity compared to the starting polypeptide. Preferably the humanized antibody monoclonal antibody that specifically binds JEV retains the ability to bind antigen compared to the nonvariant polypeptide, for instance, the binding capability is no worse than about 20 fold, for instance, no worse than about 5 fold of that of the nonvariant polypeptide. The binding capability of the humanized antibody can be determined using techniques such as fluorescence activated cell sorting (FACS) analysis or radioimmunoprecipitation (RIA), for example. The ability of the humanized antibody to bind an FcR can be evaluated. Where the FcR is a high affinity Fc receptor, such as FcγRI, FcRn or FcγRIIIA-V158, binding can be measured by titrating monomeric humanized antibody and measuring bound humanized antibody using an antibody that specifically binds to the humanized antibody in a standard ELISA format.

VI. Labeled Humanized Antibodies

The human monoclonal antibodies specific for JEV described herein can be conjugated to a therapeutic agent Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell. Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The humanized monoclonal antibodies or antibody fragments that specifically bind JEV disclosed herein can be derivatized or linked to another molecule (such as another peptide or protein). In general, the antibodies or portion thereof is derivatized such that the binding to JEV is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

A humanized antibody that specifically binds JEV can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody also can be labeled with biotin, and detected through indirect measurement of avidin or streptavidin binding. It should be noted that the avidin itself can be labeled with an enzyme or a fluorescent label.

An antibody can be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody can also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody also can be labeled with a radiolabeled amino acid. The radiolabel can be used for both diagnostic and therapeutic purposes. For instance, the radiolabel can be used to detect JEV by x-ray, emission spectra, or other diagnostic techniques. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol, a methyl or ethyl group, or a carbohydrate group. These groups can be useful to improve the biological characteristics of the antibody, such as to increase serum half-life or to increase tissue binding.

Toxins can be employed with the JEV-specific human monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401).

The JEV-specific antibodies described herein can also be used to target any number of different diagnostic or therapeutic compounds to cells expressing JEV on their surface. Thus, an antibody of the present disclosure can be attached directly or via a linker to a drug that is to be delivered directly to cells expressing cell-surface JEV. This can be done for therapeutic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-JEV antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels can be detected using photographic film or scintillation counters, fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VII. Pharmaceutical Compositions

Compositions are provided that include one or more of the antibodies that specifically bind JEV that are disclosed herein in a carrier. The compositions can be prepared in unit dosage forms for administration to a subject. The amount and timing of administration are at the discretion of the treating physician to achieve the desired purposes. The antibody can be formulated for systemic or local (such as inhalational) administration. In one example, the antibody that specifically binds JEV is formulated for parenteral administration, such as intravenous or intramuscular administration.

The compositions for administration can include a solution of the antibody that specifically binds JEV dissolved in a pharmaceutically acceptable carrier, such as an aqueous carrier. A variety of aqueous carriers can be used, for example, buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous or intramuscular administration includes about 100 mg to about 5 g of antibody per subject per day. Dosages from 200 mg up to about 15 g of antibody per subject per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies can be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 5 to 300 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 50 mg/kg can be infused over a period of some 90 minutes, followed by weekly maintenance doses for 4-8 weeks of 5 mg/kg infused over a 30 minute period if the previous dose was well tolerated.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga (1995) *Therapeutic Peptides and Proteins: Formulation, Processing, and Delivery Systems*, Technomic Publishing Company, Inc., Lancaster, Pa. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter (1994) *Colloidal Drug Delivery Systems*, J. Kreuter, ed., Marcel Dekker, Inc., New York, N.Y., pp. 219-342; and Tice & Tabibi (1992) *Treatise on Controlled Drug Delivery*, A. Kydonieus, ed., Marcel Dekker, Inc. New York, N.Y., pp. 315-339.

Polymers can be used for ion-controlled release of the antibody compositions disclosed herein. Various degradable and nondegradable polymeric matrices for use in controlled drug delivery are known in the art (Langer (1993) *Accounts Chem. Res.* 26:537-542). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., (1992) *Pharm. Res.* 9:425-434; and Pec et al., (1990) *J. Parent. Sci. Tech.* 44(2):58-65). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., (1993) *Liposome Drug Delivery Systems*, Technomic Publishing Co., Inc., Lancaster, Pa.). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

VIII. Methods of Treatment and Prophylaxis

The humanized antibodies disclosed herein can be used for the prophylaxis or treatment of a mammal, for instance, a human subject who has been diagnosed with JEV infection, or a person at risk for exposure to JEV. In some embodiments, the antibody that specifically binds JEV is administered to treat or inhibit the development of JEV infection. In these applications, a therapeutically effective amount of an antibody is administered to a subject in an amount sufficient to treat the JEV infection. In other embodiments, the antibody is administered to a subject at risk for exposure to JEV in order to inhibit the development of JEV infection. Suitable subjects can include those diagnosed with a JEV infection, a subject suspected of having contracted JEV, or a subject at risk for exposure to JEV, for instance a health care worker or other subject who lives in or travels to an area where JEV is endemic. Any active form of the antibody can be administered, including Fab and F(ab')2 fragments.

The humanized antibody is administered by any suitable means, including parenteral, subcutaneous, intraperitoneal, intrapulmonary, and intranasal. Parenteral infusions include intramuscular, intravenous, intracerebral, intraarterial, intraperitoneal, or subcutaneous administration. In addition, the humanized antibody is suitably administered by pulse infusion, particularly with declining doses of the humanized antibody. In some embodiments, the dosing is given by injections, most preferably intravenous or intramuscular injections, depending in part on whether the administration is brief or chronic.

For the prevention or treatment of disease, such as JEV infection, the appropriate dosage of humanized antibody will depend on the severity and course of the disease, whether the humanized antibody is administered for preventive or therapeutic purposes, previous prophylaxis and therapy, the subject's clinical history and response to the humanized antibody, and the discretion of the attending physician. A therapeutically effective amount of the antibody is that which provides either subjective relief of a symptom(s) or an objectively identifiable improvement as noted by the clinician or other qualified observer. These compositions can be administered in conjunction with another agent, such as an anti-viral agent, either simultaneously or sequentially. The antibodies also can be used or administered as a mixture, for example in equal amounts, or individually, provided in sequence, or administered all at once.

Single or multiple administrations of the compositions are administered depending on the dosage and frequency as required and tolerated by the subject. The composition should provide a sufficient quantity of at least one of the antibodies disclosed herein to effectively treat the subject or inhibit the development of JEV infection. The dosage can be administered once but can be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of a JEV infection without producing unacceptable toxicity to the patient.

In one embodiment, the antibody is a humanized monoclonal antibody that binds JEV, wherein the antibody has a variant Fc region, and is used for passive immunization against a disease complicated by antibody-dependent enhancement. Antibody-dependent enhancement, a phenomenon in which viral replication is increased rather than decreased by immune sera, has been observed for a large number of viruses of public health importance, including flaviviruses, coronaviruses, and retroviruses.

For passive immunization with an antibody, about 5 mg/kg to 250 mg/kg (for instance, 50-100 mg/kg) of humanized antibody is an initial candidate dosage for administration to the subject, whether, for example, by one or more separate administrations, or by continuous infusion. A typical daily dosage might range from about 5 mg/kg to 250 mg/kg or more, depending on the factors mentioned above. In general, it is desirable to provide the subject with a dosage of antibody which is in the range of from about 5 mg/kg-50 mg/kg, 50 mg/kg-100 mg/kg, 100 mg/kg-300 mg/kg (body weight of recipient), although a lower or higher dosage can be administered. Dosages as low as about 5 mg/kg can be expected to show some efficacy. Additionally, a dosage of about 10 mg/kg is an acceptable dose, although dosage levels up to about 250 mg/kg are also effective, especially for therapeutic use. For repeated administrations over several days or longer, depending on the condition, the prophylaxis or treatment is sustained until a desired suppression or modification of disease symptoms occurs. However, other dosage regimens can be useful. The progress of this therapy is easily monitored by conventional techniques and assays.

The humanized antibody composition will be formulated, dosed, and administered in a fashion consistent with good medical practice. Factors for consideration in this context include the particular disorder being prevented or treated, the particular subject being treated, the clinical condition of the individual subject, the cause of the disorder, whether JEV infection is present or the subject is at risk of exposure to JEV, the site of delivery of the agent, the method of administration, the scheduling of administration, and other factors known to medical practitioners. The prophylactically or therapeutically effective amount of the humanized antibody to be administered will be governed by such considerations, and is the minimum amount necessary to prevent, ameliorate, or treat a disease or disorder. The humanized antibody can formulated with one or more anti-viral agents. The effective amount of such other agents depends on the amount of humanized antibody present in the formulation, the type of disorder or treatment, and other factors discussed above.

IX. Diagnostic Methods and Kits

A method is provided herein for the detection of the expression of JEV in vitro or in vivo. In one example, expression of JEV is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a rat, mouse, goat, pig, bird, horse, or primate. In one embodiment, the primate is macaque, chimpanzee, cynomogous, or human.

In several embodiments, a method is provided for detecting a JEV infection. Blood samples from a subject suspected of having a JEV infection contain detectable amounts of JEV protein. Thus, JEV-specific antibodies can be used to detect JEV in a blood sample from a subject to detect JEV infection in the subject, or confirm a diagnosis of JEV infection in a subject.

The disclosure provides a method for detecting JEV in a biological sample, wherein the method includes contacting a biological sample with a humanized antibody that binds JEV under conditions conducive to the formation of an immune complex, and detecting the immune complex, to detect the JEV in the biological sample. In one example, the detection of JEV in the sample indicates that the subject has a JEV infection. In another example, detection of JEV in the sample confirms a diagnosis of JEV infection in a subject.

In one embodiment, the humanized antibody that specifically binds JEV is directly labeled with a detectable label. In another embodiment, the humanized antibody that specifically binds JEV (the first antibody) is unlabeled and a second antibody or other molecule that can bind the humanized antibody that specifically binds JEV is labeled. As is well known to one of skill in the art, a second antibody is chosen that is able to specifically bind the specific species and class of the first antibody. For example, if the first antibody is a humanized IgG, then the secondary antibody can be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, JEV can be assayed in a biological sample by a competition immunoassay utilizing JEV standards labeled with a detectable substance and an unlabeled humanized antibody that specifically binds JEV. In this assay, the biological sample, the labeled JEV standards and the humanized antibody that specifically bind JEV are combined and the amount of labeled JEV standard bound to the unlabeled antibody is determined. The amount of JEV in the biological sample is inversely proportional to the amount of labeled JEV standard bound to the antibody that specifically binds JEV.

The immunoassays and methods disclosed herein can be used for a number of purposes. In one embodiment, the humanized antibody that specifically binds JEV can be used to detect the production of JEV in cells in cell culture. In another embodiment, the antibody can be used to detect the amount of JEV in a biological sample. Increased expression of JEV is associated with the severity of JEV infection. In one embodiment, a kit is provided for detecting JEV in a biological sample, such as a blood sample or tissue sample.

For example, to confirm a JEV infection diagnosis in a subject, a blood sample can be obtained to detect the presence of JEV protein. Kits for detecting a polypeptide will typically include a humanized antibody that specifically binds JEV, such as any of the antibodies disclosed herein. In some embodiments, an antibody fragment, such as an Fv fragment or a Fab is included in the kit. In a further embodiment, the antibody is labeled (for example, with a fluorescent, radioactive, or an enzymatic label).

In one embodiment, a kit includes instructional materials disclosing means of use of an antibody that specifically binds JEV. The instructional materials can be written, in an electronic form (such as a computer diskette or compact disk) or can be visual (such as video files). The kits can also include additional components to facilitate the particular application for which the kit is designed. Thus, for example, the kit can additionally contain means of detecting a label (such as enzyme substrates for enzymatic labels, filter sets to detect fluorescent labels, appropriate secondary labels such as a secondary antibody, or the like). The kits can additionally include buffers and other reagents routinely used for the practice of a particular method. Such kits and appropriate contents are well known to those of skill in the art.

In one embodiment, the diagnostic kit includes an immunoassay. Although the details of the immunoassays can vary with the particular format employed, the method of detecting JEV in a biological sample generally includes the steps of contacting the biological sample with an antibody which specifically reacts, under immunologically reactive conditions, to a JEV polypeptide. The antibody is allowed to specifically bind under immunologically reactive conditions to form an immune complex, and the presence of the immune complex (bound antibody) is detected directly or indirectly.

Any of the humanized antibodies that specifically bind JEV, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Disclosed herein are humanized antibodies that specifically bind JEV and/or a JEV envelope polypeptide. These antibodies can be used to detect a JEV infection, or can be used to passively immunize a subject against JEV.

Like other flaviviruses, JEV contains a single-stranded RNA genome that codes for the three virion proteins, for instance, the capsid (C), pre-membrane/membrane (prM/M) and envelope (E) proteins and seven non-structural proteins (NS1, NS2A, NS2B, NS3, NS4A, NS4B and NS5). The E protein is the major protective antigen, eliciting neutralizing antibodies that play an important role in protective immune responses. In the replication cycle, the E protein mediates virus attachment to putative cell receptor(s) and viral fusion with the endosomal membranes. Three-dimensional structures of several flavivirus E's have been determined by x-ray crystallography (Kanai et al., (2006) *J Virol* 80:11000-8; Modis et al., (2003) *Proc Natl Acad Sci USA* 100:6986-91; Modis et al., (2005) *J Virol* 79:1223-31; Rey et al., (1995) *Nature* 375:291-8). The head-to-tail dimers of E are tightly organized on the virion surface. The monomeric E is folded into three structurally distinct domains (domain I-III). Domain III adopts an immunoglobulin-like structure consisting of seven anti-parallel β-strands. This domain is linked by a flexible region to domain I, which folds into an eight-stranded anti-parallel β-barrel. Domain I contains approximately 120 amino acids in three segments disrupted by two inserts in the form of looped sequences, which together form the dimerization domain (domain II). At the distal end of one of these domain II inserts is a flavivirus-conserved peptide shown to be involved in membrane fusion (Rey et al., (1995) *Nature* 375:291-8; Kuhn et al., (2002) *Cell* 108:717-25; Rey et al., (1995) *Nature* 375:291-8).

Studies of mouse monoclonal antibodies from flavivirus infections have provided much information about E functional specificities and antigenic structures. A majority of cross-reactive, weakly- to non-neutralizing antibodies react with epitope determinants involving the fusion peptide in domain II (Stiasny et al., (2006) *J Virol* 80:9557-68). Antibodies that recognize domain III epitopes are type-specific and efficient neutralizers of viral infection (Oliphant et al., (2005) *Nat Med* 11:522-30; Roehrig (2003) *Adv Virus Res* 59:141-75). Domain III-reactive antibodies can neutralize the virus at an early infection step presumably by blocking viral attachment to cell receptors or by interfering conformational changes to E, thereby preventing membrane fusion (Crill & Roehrig (2001) *J Virol* 75:7769-73; Nybakken et al., (2005) *Nature* 437:764-9). Mouse monoclonal antibodies that neutralize flaviviruses, such as SLEV, yellow fever virus and dengue virus at high titers in vitro, have also been shown to mediate protection of infection in vivo (Brandriss et al., (1986) *J Gen Virol* 67 (Pt 2):229-34; Roehrig et al., (2001) *Ann N Y Acad Sci* 951:286-97). In the case of JEV, studies have shown that passive transfer of mouse MAbs can protect against prior and subsequent infection in mice, goats and monkeys (Kimura-Kuroda & Yasui (1988) *J Immunol* 141:3606-10; Zhang et al., (1989) *J Med Virol* 29:133-8). However, the possible immunogenicity of these antibodies limits their clinical utility in humans. Only relatively few monoclonal antibodies that efficiently neutralize flaviviruses and map to domain I or II have been characterized (Daffis et al., (2005) *Virology* 337:262-72; Holzmann et al., (1997) *J Gen Virol* 78 (Pt 1):31-7; McMinn et al., (1995) *Virology* 211:10-20; Morita et al., (2001) *Virology* 287:417-26; Ryman et al., (1997) *J Gen Virol* 78 (Pt 6):1353-6). Consequently, the antigenic structures of these domains and their involvement in the protective immune response remain poorly understood.

There has been a lack of primate-derived antibodies for characterization of flavivirus antigenic epitopes discovered with mouse antibodies. However, dengue virus (DENY) type-specific and cross-reactive antibodies recently have been recovered from infected chimpanzees by repertoire cloning. A DENV-4-specific, highly neutralizing monoclonal antibody (5H2) has been shown to react with epitope determinants in domain I and a DENV cross-reactive antibody (1A5) was shown to react with the fusion peptide in domain II (Lai et al., (2007) *J Virol.* 81:12766-74; Goncalvez et al., (2004) *J Virol* 78:12919-28). It was also demonstrated that passively transferred MAb 1A5, which shares characteristics with a major subset of flavivirus cross-reactive antibodies, up-regulates dengue virus replication by a mechanism of antibody-dependent enhancement (Goncalvez et al., (2007) *Proc Natl Acad Sci USA* 104:9422-7.). Passive transfer with the highly-neutralizing antibody MAb 5H2 has been shown to protect mice and monkeys against DENV-4 challenge (Lai et al., (2007) *J Virol.* 81:12766-74).

Disclosed herein is the repertoire cloning, epitope mapping and functional characterization of JEV-neutralizing MAbs from immunized chimpanzees. Several panning strategies were applied to recover Fabs that bind to epitopes in different antigenic domains. Representative MAbs that neutralized JEV efficiently and mapped to each of the three domains in E were selected for analysis of binding activities for JEV and evaluation of their in vitro neutralizing titers against strains belonging to the four JEV genotypes. As proof of concept, the protective capacities of these humanized antibodies were analyzed in a mouse model of Japanese encephalitis.

Example 1

Materials and Methods

This Example describes materials and methods that were used in performing Examples 2-10. Although particular methods are described, one of skill in the art will understand that other, similar methods also can be used.

Viruses and Cultured Cells

Simian Vero cells and mosquito C6/36 cells were grown in Minimum Essential Medium (MEM). Schneider's *Drosophila* Line 2 (S2) cells were cultured in Schneider's *Drosophila* medium and human embryonic kidney 293 T cells were cultured in Dulbecco's Modified Essential Medium (DMEM). All media were supplemented with 10% fetal bovine serum (FBS), 0.05 mg/ml gentamycin, and 2.5 units/ml fungizone. Media were purchased from Invitrogen (Carlsbad, Calif.), and cells were from the American Type Culture Collection (Manassas, Va.). The inactivated JEV vaccine, JE-VAX®, was obtained from Sanofi Pasteur Inc. (Swiftwater, Pa.). The attenuated JEV SA14-14-2 strain was provided by K. Eckels and R. Putnak. The JEV stock used for infection of chimpanzees, phage library panning, and plaque reduction neutralization tests (PRNT) was prepared from infected C6/36 cells grown in VP-SFM medium (Invitrogen). The virus titer was approximately $10^8$ focus forming units (FFU)/ml as determined on Vero cell monolayers. PRNT using the four genotype strains of wild type JEV was performed at the Center for Vaccine Development, Mahidol University (Nakhonpathom, Thailand). These strains were JE 1991 (genotype I), JE B 1034/8 (genotype II), Beijing (genotype III) and JKT 9092 (genotype IV). The JEV prototype strain Nakayama, belonging to genotype II, was used for mouse challenge experiments performed at Adimmune Corporation (Taichung, Taiwan). Experiments to detect antibody-binding specificities were performed by ELISA with DENV-1 (Hawaii), DENV-2 (New Guinea B), DENV-3 (H87), DENV-4 (814669), Langat virus (LGTV) strain TP 21, and WNV/DENV-4 chimera as described previously (Goncalvez et al., (2004) *J Virol* 78:12910-8).

Antibodies

Humanized MAbs 1A5 and 5H2 derived from chimpanzee Fabs were prepared by transient transfection of 293 T cells (Goncalvez et al., (2004) *J Virol* 78:12910-8; Men et al., (2004) *J Virol* 78:4665-74; Kemp Biotechnology, Gaithersburg, Md.). Hyperimmune mouse ascites fluid (HMAF) raised against JEV was purchased from American Type Culture Collection (Manassas, Va.). Mouse JEV complex-reactive MAb 8743 (MAb 6B4A-10) was purchased from Chemicon (Temecula, Calif.). JEV E domain III-specific mouse MAb E3.3 was provided by S-C Wu (Lin et al., (2003) *J Virol* 77:2600-6).

JEV E Antigen Preparations

Three different E antigen preparations from JEV SA14-14-2 were used: (i) JEV virions; (ii) domain III-specific E; and (iii) N-terminal 80% E. To prepare JEV virions, mosquito C6/36 cells grown in MEM plus supplements were infected with the virus at 0.1 multiple of infection (MOI) in VP-SFM medium (Invitrogen, Carlsbad, Calif.), and incubated at 32° C. The culture medium was harvested eight days after infection and kept frozen at −80° C. The virus preparation was used for panning, ELISA and neutralization assays, as well as for selection of neutralization-escape variants. The recombinant domain III-specific E was constructed for use as panning antigen. The protein was expressed in bacteria with a histidine tag, essentially as described (Jaiswal et al. (2004) *Protein Expr Purif* 33:80-91; Wu et al., (2003) *Vaccine* 21:2516-22). The DNA sequence corresponding to amino acids 296-398 (DIII) near the C-terminus of E was amplified by PCR from the viral cDNA of JEV SA 14-14-2. The DNA product was then purified, digested with EcoRI and HindIII, followed by insertion into the pET21 cloning vector (Novagen, Madison, Wis.). *Escherichia coli* (strain BL21 (DE3)) was transformed with pET21 plasmid containing the insert. The histidine-tagged, domain III E protein was affinity-purified through a column of TALON® Metal Affinity Resin (Clontech, Mountain View, Calif.). Western blot analysis and ELISA were performed using JEV HMAF and MAb E3.3 to confirm the identity and proper folding of the recombinant domain III E protein.

Recombinant 80% E was generated in *Drosophila* S2 cells essentially as described in Ledizet et al., (2005) *Vaccine* 23:3915-24; Men et al., (1991) *J Virol* 65:1400-7; Putnak et al., (2005) *Vaccine* 23:4442-52. The DNA encoding amino acids 131-692 of the PrM/N-terminal 80% E fusion protein was amplified by PCR from JEV cDNA using the primers

```
                                       (SEQ ID NO: 7)
GGAGCCATGAAGAGATCTAATTTCCAGGGG
and (SEQ ID NO: 8)
GCCCAGCGTGCTCCGCGGTTTGTGCCAATGGTG.
```

The DNA product was digested with BglII and SacII and inserted into the pMTBiP/V5-HisB expression vector (Invitrogen, Carlsbad, Calif.). The recombinant plasmid and a blasticidin-resistance plasmid, pCoBlast were co-transfected into *Drosophila* S2 cells according to *Drosophila* Expression System Kit (Invitrogen, Carlsbad, Calif.). Stably-transformed cells were selected with blasticidin and then transferred to *Drosophila* Serum-Free Medium (Invitrogen, Carlsbad, Calif.). Cultured S2 cells expressing JEV prM-80% E were induced with $CuSO_4$ at 500 μM. The secreted 80% E protein is immediately followed by the V5 epitope flag and poly-histidine tag encoded by the plasmid vector. The recombinant E protein was affinity-purified with TALON® Metal Affinity Resin. Western blot analysis and ELISA were performed with HMAF, MAb E3.3 and MAb 8743 to verify the identity of recombinant E. Variants of recombinant 80% E containing single amino acid substitutions were constructed using QuikChange® Site-Directed Mutagenesis Kit (Stratagene, La Jolla, Calif.).

Immunization of Chimpanzees with JEV Vaccines and Construction of γ1/κ Antibody Library Two chimpanzees (96A007 and 1620) were administered subcutaneously (sc) three doses of JE-VAX® of 1 ml each at days 0, 7, and 30, according to the regimen indicated. One year later the chimpanzees were infected with a mixture of attenuated JEV strain SA14-14-2 and WNV/DENV-4 chimera each at $10^6$ FFU, diluted in MEM plus 0.25% human serum albumin to boost the antibody response. Eight weeks after infection, bone marrow was aspirated from each chimpanzee and the lymphocytes were prepared by centrifugation on a Ficoll-Paque gradient. Repertoire cloning of chimpanzee Fab fragments was performed as previously described (Men et al., (2004) *J Virol* 78:4665-74). Approximately $1 \times 10^7$ bone marrow lymphocytes from chimpanzee 96A007, which developed a higher JEV-neutralizing antibody titer than did chimpanzee 1620, were used for phage library construction. A library with a diversity of $2 \times 10^8 \sim 1 \times 10^9$ was obtained at each cloning step.

Panning of Phage Library and Selection of JEV-specific Fabs

The pComb 3H DNA library that contained the $V_L$-$C_L$ and $V_H$-$C_{H1}$ inserts was used for phage preparation as previously described (Men et al., (2004) *J Virol* 78:4665-74). To increase the possibility of recovering antibodies against different epitopes on the JEV E, three different panning strategies were used. The phage library was first panned using JEV virions captured by chimpanzee convalescent sera coated on the wells of an ELISA plate. Panning of the phage library by epitope masking also was conducted as described (Ditzel et al., (1995) *J Immunol* 154:893-906). Briefly, wells of a microtiter plate coated with JEV virions were incubated with purified Fab A3 (isolated in panning described above) at a concentration of 50 µg/ml for 1 hour at 37° C. One-fourth of volume was removed before adding 50 µl of the phage library. The third strategy of antibody selection was performed using domain III-specific E as panning antigen. Briefly, wells of a 96-well ELISA plate were coated with 5 µg/well of purified domain III E in 0.1 M carbonate buffer, pH 9.0. After washing with phosphate buffered saline (PBS), antigen-coated wells were blocked with 3% bovine serum albumin (BSA). The phage library was then added as described. Following three cycles of panning in each case, the selected phage population was used for infection of *E. coli* XL-1 to produce phagemid DNA. Phagemid DNA was cleaved with SpeI and NheI to remove the phage gene III segment and circularized for transformation of *E coli* XL-1. Transformed *E. coli* colonies were screened by ELISA to identify clones producing soluble Fab fragments reactive with JEV. Individual Fabs were prepared and screened for binding specificity to JEV virions or domain III E. Plasmids were sequenced to identify Fab clones with distinct $V_H$ and $V_L$ DNA inserts.

Production of Fabs and Humanized MAbs

The histidine-tagged Fab produced in *E. coli* was affinity-purified using TALON® Metal Affinity Resin. The Fab purity was analyzed by SDS-PAGE and the concentration determined using BCA Protein Assay Kit (Pierce, Rockford, Ill.). Construction of plasmids for expression of full-length humanized IgG1 (designated as MAb thereafter) from cloned Fab DNA was carried out as described (Men et al., (1991) *J Virol* 65:1400-7). MAb expression was verified by transfection of 293T cells (purchased from ATCC) in the presence of Lipofectamine (Invitrogen, Carlsbad, Calif.) and grown in OPTIMEM® medium. One day after transfection, cells were washed and DMEM was added. Cells were incubated for 5-7 days and the culture medium was harvested. The medium was concentrated and the MAb product was purified on a protein A column (Pierce, Rockford, Ill.). Scale-up MAb production was performed by Kemp Biotechnology (Gaithersburg, Md.).

Measurement of Neutralizing Titers of Fab and MAb

The neutralizing titer of Fab or MAb was determined by PRNT against the representative JEV strains essentially as described (Men et al., (1991) J Virol 65:1400-7; Okuno et al., (1985) *Brief report. Arch Virol* 86:129-35). Virus foci that formed on the cell monolayer were immuno-stained and the antibody $PRNT_{50}$ titer in µg/ml was calculated.

Biotinylation of Purified Fab and Competition ELISA

Purified Fabs were biotinylated with EZ-Link NHS-LC-Biotin (Pierce, Rockford, Ill.) and used in competition ELISA. Briefly, biotin-labeled Fab at a fixed concentration was mixed with dilutions of a crude or purified preparation of competing Fab. The mixture was added to JEV virion-coated wells and incubated at 37° C. After washing, streptavidin-alkaline phophatase (Pierce, Rockford, Ill.) was added to detect the amount of biotinylated Fab attached to the virus.

Measurement of Binding Affinity

Affinity binding analysis by ELISA or surface plasmon resonance (SPR) biosensor was performed to determine the Fab or MAb binding activity for JEV virions. ELISA was performed as described previously with minor modifications, i.e., in the absence of detergent at all steps (11, 47). JEV HMAF was used to coat the microtiter plate. Following blocking with 3% BSA, JEV at a pre-determined concentration was added and incubated at 37° C. for 1 hour. Dilutions of affinity-purified Fab were added and incubated at 37° C. for 1 h. The Fab bound to JEV on the microtiter plate was detected using a goat anti-human IgG-alkaline phosphatase conjugate (Sigma, St. Louis, Mo.). The steady-state equilibrium affinity constant ($K_D$) was calculated as the Fab concentration that produced 50% maximum binding.

The SPR biosensor experiments were conducted using a Biacore 3000 instrument (Biacore Inc, Piscataway, N.J.) with short carboxy-methylated dextran sensor surfaces (CM3; GE Healthcare, Piscataway, N.J.) and standard amine coupling as described (Schuck et al., (1999) *Current protocols in protein science*. New York: John Wiley & Sons 2:20.2.1-20.2.21). Since the recombinant E protein showed self binding in preliminary experiments, the E protein was immobilized on the chip surface and the kinetics of Fab binding and dissociation were recorded for 40 to 50 minutes and 2 hours to 10 hours, respectively, at various Fab concentrations (Schuck (1997) *Annu Rev Biophys Biomol Struct* 26:541-566). Analysis of antibodies was conducted at a flow rate of 2 µl/min for Fab B2 and 5 µl/min for Fabs A3 and E3, using PBS-P buffer (137 mM NaCl, 2.7 mM KCl, 10 mM $Na_2HPO_4$, 2.3 mM $KH_2PO_4$, 0.005% surfactant P20, pH 7.4) at 25° C. The chip surface was regenerated with 0.05% Triton X 100/2M NaCl in the case of Fab B2. No regeneration conditions were applied with Fabs A3 and E3. The kinetic traces were globally fitted with a model for continuous ligand distributions combined with a two-compartment approximation of mass transport (Svitel et al., (2007) *Biophys J* 92:1742-58.).

Immunoprecipitation and Western Blot Analysis

Immunoprecipitation was performed with lysates of JEV-infected mosquito cells or purified recombinant E. C6/36 cells were infected with the virus at MOI of 1 and incubated for 5 days at 32° C. Infected cells were rinsed with PBS and added lysis buffer containing 1% NP-40, 0.15 M NaCl and 0.1 M Tris, pH 7.5. The cell lysate or recombinant E was incubated with the test antibody for 2 hours at 4° C. A 10-µl suspension of protein A Sepharose beads (Calbiochem, La Jolla, Calif.) was added and the mixture incubated overnight at 4° C. The beads containing immunocomplexes were collected by centrifugation and washed three times with the lysis buffer. The immunocomplexes were added with 4× loading buffer (Invitrogen, Carlsbad, Calif.) and separated by SDS-PAGE. After transferring onto a nitrocellulose membrane, the E protein was detected by a mouse or humanized anti-JEV antibody followed by anti-mouse or anti-human IgG-HRP (Pierce, Rockford, Ill.), or by a mouse anti-V5 epitope MAb-HRP conjugate (Invitrogen, Carlsbad, Calif.) for chemiluminescence development (Pierce, Rockford, Ill.).

Selection of JEV Antigenic Variants

Affinity-purified Fabs A3, B2 and E3 were used for selection of neutralization-escape mutants (Goncalvez et al., (2004) *J Virol* 78:12919-28). Briefly, approximately $1 \times 10^7$ FFU of parental JEV SA14-14-2 were mixed with 25 μg/ml of Fab in MEM and incubated at 37° C. for 1 hour. The mixture was added to the Vero cell monolayer and incubated at 37° C. for 1 hour. Following removal of the inoculum, the plate was rinsed once with PBS, refed with 3 ml of MEM containing 2% FBS and 5 μg/ml of the selecting Fab, and incubated at 37° C. for 5 days. Antibody-resistant variants were isolated by plaque-to-plaque purification on Vero cells and the individual isolates were amplified in infected C6/36 cells in the presence of the selecting Fab. Sequence analysis of JEV antigenic variants was conducted as described previously (Kanai et al. (2006) *J Virol* 80:11000-8). The JEV E structure modeling was performed with the crystal coordinates of WNV, accession code 2169 as a template (Kimura-Kuroda & Yasui (1988) *J Immunol* 141:3606-10), and SwissModel (Guex & Peitsch (1997) *Electrophoresis* 18:2714-23; Peitsch (1996) *Biochem Soc Trans* 24:274-9). Graphical development was performed using the UCSF Chimera package from the Resource for Biocomputing, Visualization, and Informatics (University of California, San Francisco).

Mouse Model for JEV Challenge

For analysis of efficacy, groups of 4-week-old inbred ddy mice (either sex, n=12) were infused with 0.5 ml of MAb at doses of 200, 100, 40, 20, 8, 1.6 or 0.32 μg per mouse by the intraperitoneal route (i.p.) and the control group received PBS diluent only. One day later, mice in all groups were challenged by the intracerebral (i.c.) route with a diluent containing 40×50% lethal dose ($LD_{50}$) (1.5 FFU) of JEV strain Nakayama in 30 μl. The animals were monitored daily for clinical signs of infection, including ruffled hair, hunched back, paralysis and death for two weeks. When signs of encephalitic paralysis developed, mice were euthanized as the experiment end-point. In the infection-intervention experiment by passive antibody transfer, a single dose of test MAb at 200 μg was administered by the i.p. route at days 1, 3 or 5 following i.c. inoculation of $40 \times LD_{50}$ JEV Nakayama. Mice were monitored daily for symptoms of encephalitis for three weeks. Student's t test was used to compare the average survival time (AST) between the mouse groups that received MAb and those that received PBS.

Example 2

Chimpanzee Antibody Response to JEV Vaccines and Isolation of Fabs

This Example describes the immunization of chimpanzees with the JEV vaccine, JE-VAX, the resulting antibody response, and the isolation of Fabs using three different panning strategies.

Two chimpanzees were initially immunized with three doses of inactivated vaccine JE-VAX®. After two months chimpanzees 96A007 and 1620 developed only moderate $PRNT_{50}$ titers against JEV SA14-14-2 (1/100 and 1/71, respectively). After inoculation with a mixture of JEV SA14-14-2 and WNV/DENV-4 chimera, high JEV-neutralizing antibody titers 1/10633 and 1/3114 were detected in the serum of chimpanzees 96A007 and 1620, respectively. Chimpanzee bone marrow was aspirated eight weeks after infection and the cells of chimpanzee 96A007 were used for a phage library construction.

Selection of Fabs from a combinatorial library with a single panning antigen often yields only a dominant antibody subset that can or can not be neutralizing. Highly neutralizing antibodies can be present as a minor subset. Therefore, three different panning strategies were performed in order to assemble a collection of JEV-neutralizing Fab antibodies for further functional characterizations.

Fabs Recovered from Panning with JEV Virions (Group 1 Fabs)

Figure 1:
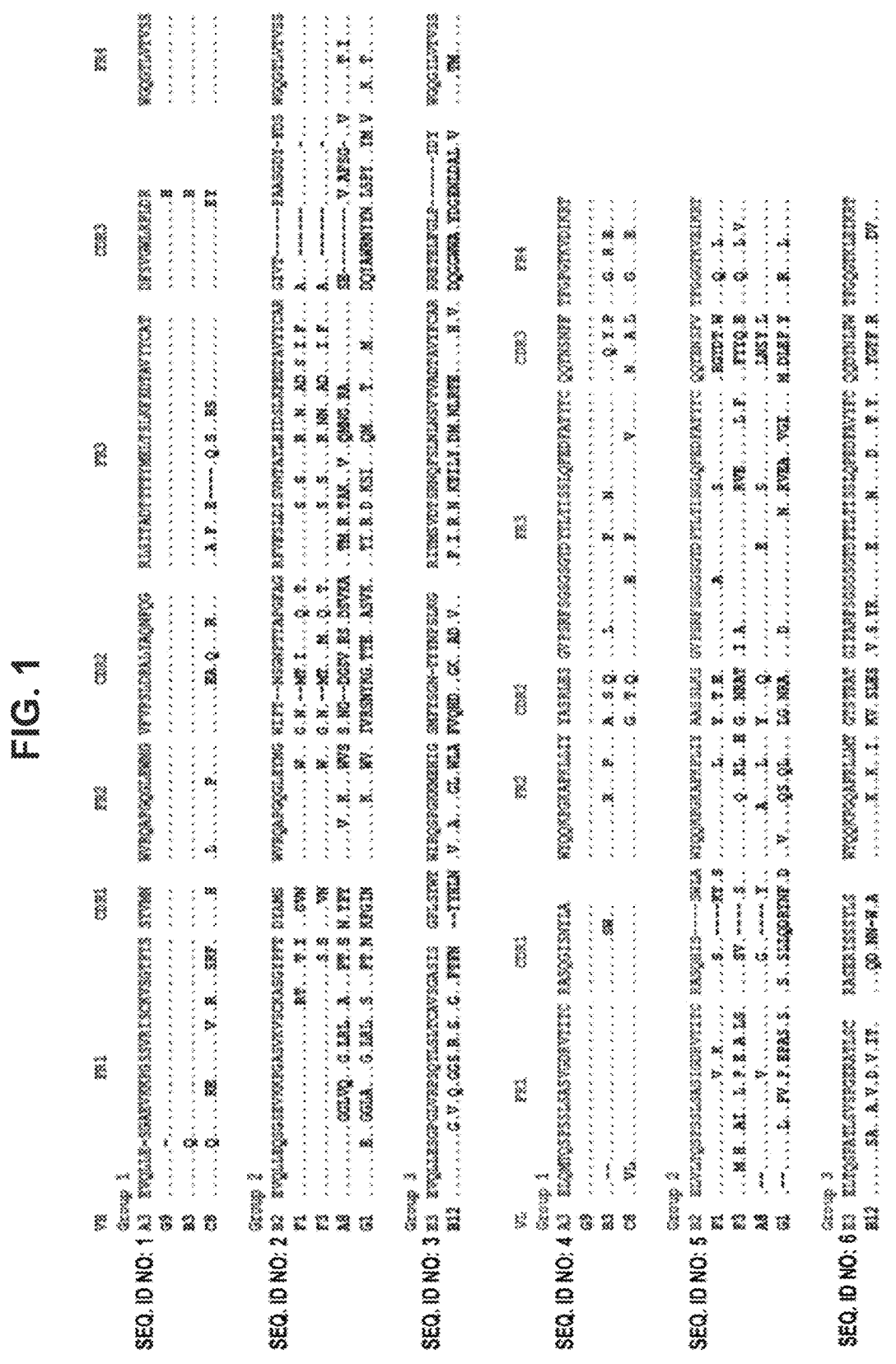

The phage library was first panned with JEV virions captured by chimpanzee polyclonal sera. A total of 200 *E. coli* clones were screened for Fabs reactive to the virus. Sequence alignment of 48 positive Fab clones identified four $V_H$ sequences, three of which, i.e., Fabs A3, G9 and B3, were similar but not identical (FIG. 1). These Fabs appeared to represent a dominant subset of antibodies in the library. The $V_L$ sequences of these four Fab clones showed three distinct patterns. Binding assay by ELISA showed that, with the exception of Fab A3, which was weakly reactive to WNV (detected only at 1/10 dilution), the other three Fabs reacted with JEV, but not with DENY-1 to -4, WNV or LGTV. These Fabs neutralized JEV efficiently at $PRNT_{50}$ titers ranging from 2.55 to 7.91 nM (0.12 to 0.36 μg/ml; Table 2).

TABLE 2

JEV-neutralizing Fabs recovered by different panning strategies

| Group (panning antigen) | Fab | $PRNT_{50}$ titer (nM)[a] | ELISA titer ($1/\log_{10}$ dilution) binding of[b]: | |
|---|---|---|---|---|
| | | | JEV | Other flaviviruses[c] |
| 1 (JEV SA14-14-2) | A3 | 2.55 ± 0.42 | 4.7 | <1 |
| | B3 | 4.14 ± 0.65 | 4.5 | <1 |
| | G9 | 4.38 ± 1.10 | 4.4 | <1 |
| | C8 | 7.91 ± 3.29 | 4.3 | <1 |
| 2 (masking with Fab A3) | B2 | 0.25 ± 0.09 | 4.2 | <1 |
| | F1 | 0.41 ± 0.21 | 4.1 | <1 |
| | F3 | 0.45 ± 0.22 | 4.2 | <1 |
| | A8 | >1,100 | 4.2 | <1 |
| | G1 | >1,040 | 3.0 | <1 |
| 3 (recombinant DIII E) | E3 | 84.90 ± 20.2 | 4.2 | <1 |
| | B12 | >1,070 | 4.0 | <1 |

[a] 1 nM = ~0.046 μg/ml.
[b] Microtiter plates were coated with virions of the indicated flavivirus ($10^6$ FFU/ml). The ELISA titer was the $\log_{10}$ reciprocal dilution of Fab that gave an optical density reading twofold or greater than the background. The initial Fab concentration was ~100 μg/ml.
[c] DENV-1, DENV-2, DENV-3, DENV-4, WNV, and LGTV were tested.
Non-neutralizing Fabs A8, G1, and B12 were included for comparison.

Fabs Recovered from Panning by Epitope-masking (Group 2 Fabs)

To increase the possibility of recovering a different subset of antibodies binding to minor epitopes on E, Fab A3 (described above) was used for epitope-masking in a new panning of virions. From some 200 clones screened, 12 Fabs bound to the virus. Sequence analysis identified five $V_H$ sequences different from members of the group 1 Fabs (FIG. 1). PRNT showed that three Fabs, i.e., B2, F1 and F3, had high neutralizing activities ranging from 0.25 to 0.45 nM (0.012 to 0.021 µg/ml), while Fabs A8 and G1 were not neutralizing (Table 2). Members of this Fab group bound to JEV, but not to DENY-1 through 4, WNV or LGTV as analyzed by ELISA.

Fabs Recovered from Panning with Domain III E (Group 3 Fabs)

Evidence indicates that flavivirus infections elicit a major class of cross-reactive, but weakly neutralizing antibodies that react with epitopes involving the fusion peptide in domain II E (Stiasny et al., (2006) *J Virol* 80:9557-68). Studies of cloning of DENY-neutralizing antibodies from chimpanzees (Goncalvez, et al., (2004) *J Virol* 78:12910-8) and of cloning WNV antibodies from humans (Throsby et al., (2006) *J Virol* 80:6982-92) have suggested that antibodies reactive to domain III E are rare. Nevertheless, studies on WNV-neutralizing antibodies indicate that domain III E is an antigenic target in the murine model (Oliphant et al., (2005) *Nat Med* 11:522-30). The third strategy to recover chimpanzee antibodies against JEV used domain III-specific E as the panning antigen. Twenty-three Fabs were identified and sequence analysis revealed two distinct $V_H$ segments, as present in Fabs E3 and B 12, with Fab E3 representing 78% of the clones. Both Fabs were JEV specific. Fab E3 neutralized the virus, at a relatively low titer (84.9 nM), compared to the neutralizing titers of Fabs selected with the previous panning strategies (Table 2). Fab B 12 did not neutralize JEV (>1070 nM).

Human Homologs of Chimpanzee Antibodies

A search for sequence homology in the data base showed the most related human IgG gene homologs of the panel of chimpanzee Fabs (Table 3). The γ1 heavy chain sequences of these Fabs demonstrated similarity to the human VH1, VH3, VH4 or VH7 gene families with sequence homologies ranging from 67 to 83%, excluding the CDR-3 regions. The κ light chain sequences exhibited most identity with human VK1, VK2 or VK3 gene families with sequence homologies of 80-95%, excluding the CDR-3 regions. The four Fabs in Group I were most related to VH1 and VK1 germ line genes. The γ1 heavy chain sequences of the most highly neutralizing Fabs in Group II had the most identity with the human VH3 gene family

TABLE 3

Sequence similarities between chimpanzee Fabs and their most closely related human immunoglobulin homologs

| | Comparison with human homolog | | | |
|---|---|---|---|---|
| | $V_H$ | | $V_L$ | |
| Chimpanzee Fab | Family (gene)[a] | % Identity[b] | Family (gene)[a] | % Identity[b] |
| Group 1 | | | | |
| A3 | VH1 (VH1-69) | 70 | VK1 | 95 |
| G9 | VH1 (VH1-69) | 70 | VK1 | 80 |
| B3 | VH1 (VH1-69) | 70 | VK1 (VK1D-16) | 91 |
| C8 | VH1 (VH1-69) | 67 | VK1 (VK1D-27) | 92 |
| Group 2 | | | | |
| G1 | VH3 (3-49RBm) | 81 | VK2 (VK2-28) | 87 |
| A8 | VH3 (VH3-74) | 82 | VK1 (VK1-9) | 95 |
| B2 | VH7 (VH7-4-1) | 83 | VK1 (VK1D-16) | 86 |
| F1 | VH7 (VH7-4-1) | 79 | VK1 (VK1D-39) | 85 |
| F3 | VH7 (VH7-4-1) | 82 | VK3 | 83 |

TABLE 3-continued

Sequence similarities between chimpanzee Fabs and their most closely related human immunoglobulin homologs

| | Comparison with human homolog | | | |
|---|---|---|---|---|
| | $V_H$ | | $V_L$ | |
| Chimpanzee Fab | Family (gene)[a] | % Identity[b] | Family (gene)[a] | % Identity[b] |
| Group 3 | | | | |
| B12 | VH3 (VH3-74) | 77 | VK1 (KV1-9) | 86 |
| E3 | VH4 | 74 | VK3 (KV3D-7) | 90 |

[a]The DNAPLOT program was used to search for the most closely related homologs of human germ line IgG genes in the database.
[b]The percent amino acid identity in the $V_H$ or $V_L$ segment, excluding the CDR-3 region, was determined with the MEGA program.

Example 3

Fab Binding Sites on JEV by Competition ELISA

This Example describes an analysis of the relatedness of the Fab binding sites on JEV using competition ELISA. Highly neutralizing Fabs A3, B2 recognized non-overlapping epitopes on JEV.

Figure 2B:
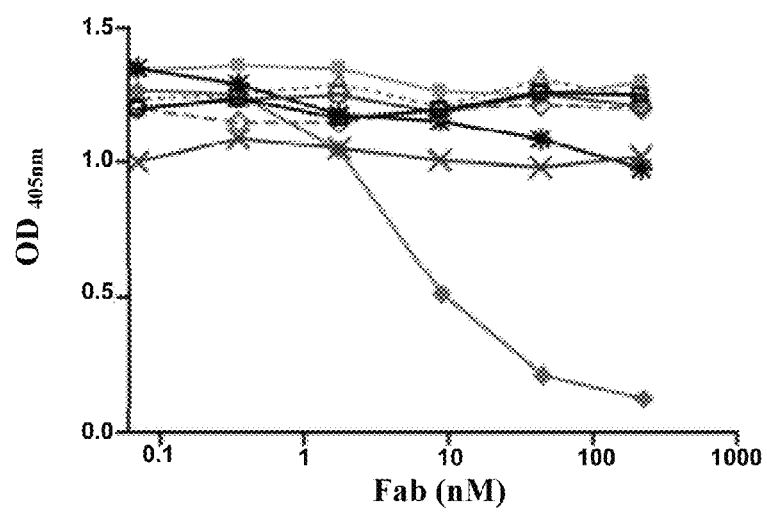
Figure 2C:
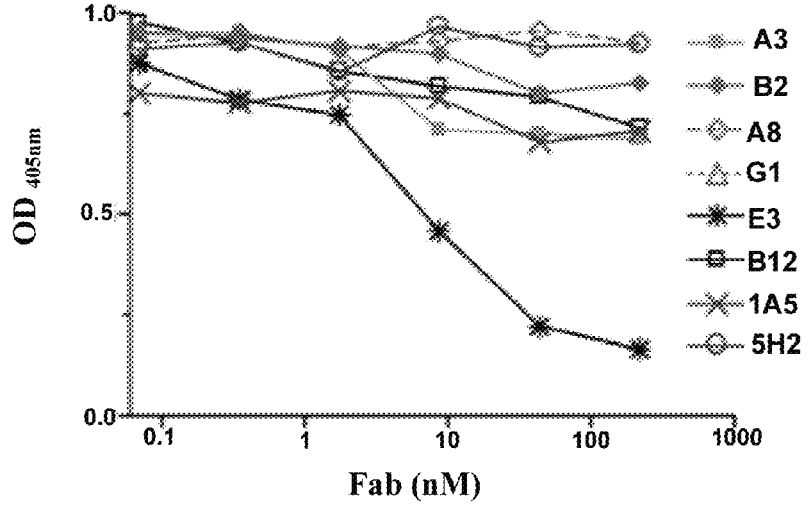

Six Fabs that were distinct in their CDR-3H sequences were selected for analysis of the relatedness of their binding sites on JEV by competition ELISA (FIG. 1). Fabs A3, B2, and E3 were representatives of the three Fab groups that neutralized JEV most efficiently. Additionally, Fabs A8 and G1 (Group 2) and Fab B12 (Group 3) were selected for analysis of their binding sites on JEV. Binding competition was not detected among these Fabs with each other, nor with DENV-4 specific Fab 5H2 as a negative control (Men et al., (2004) *J Virol* 78:4665-74; FIG. 2). Further, binding competition was not observed with Fab 1A5, a flavivirus broadly-reactive antibody that binds to the conserved fusion loop in E identified earlier (Goncalvez et al., (2004) *J Virol* 78:12919-28). Thus, highly neutralizing Fabs A3, B2 and E3 as well as non-neutralizing Fabs A8, G1 and B12 recognized non-overlapping epitopes on JEV.

Example 4

Antigenic Specificity of Fabs

This Example describes the antigenic specificity of Fabs A3, B2, and E3, as determined by Western blot.

Figure 3A:
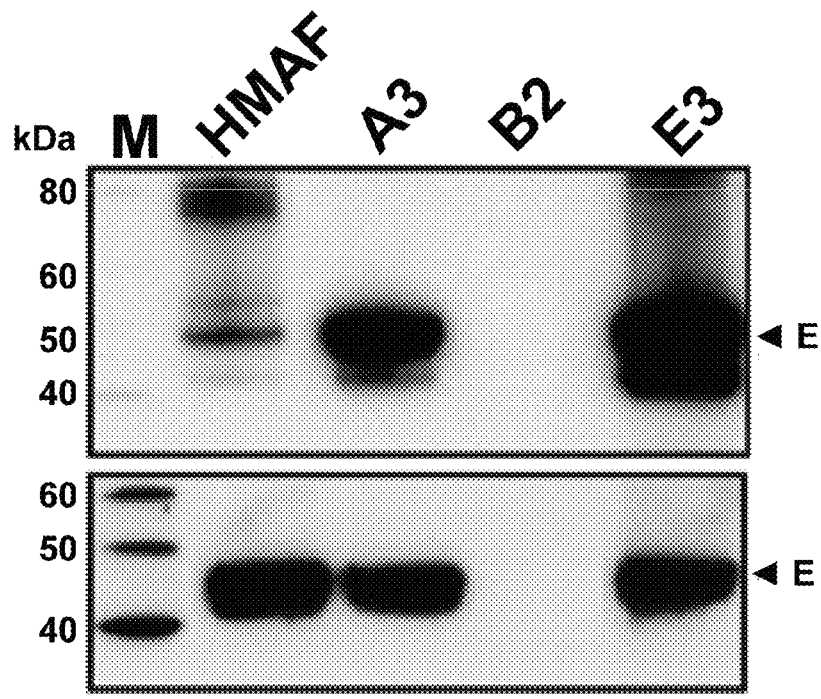
FIGS. 3A-3B are a series of digital images of gels showing the identification of E as the binding target of JEV MAbs.
Figure 3B:
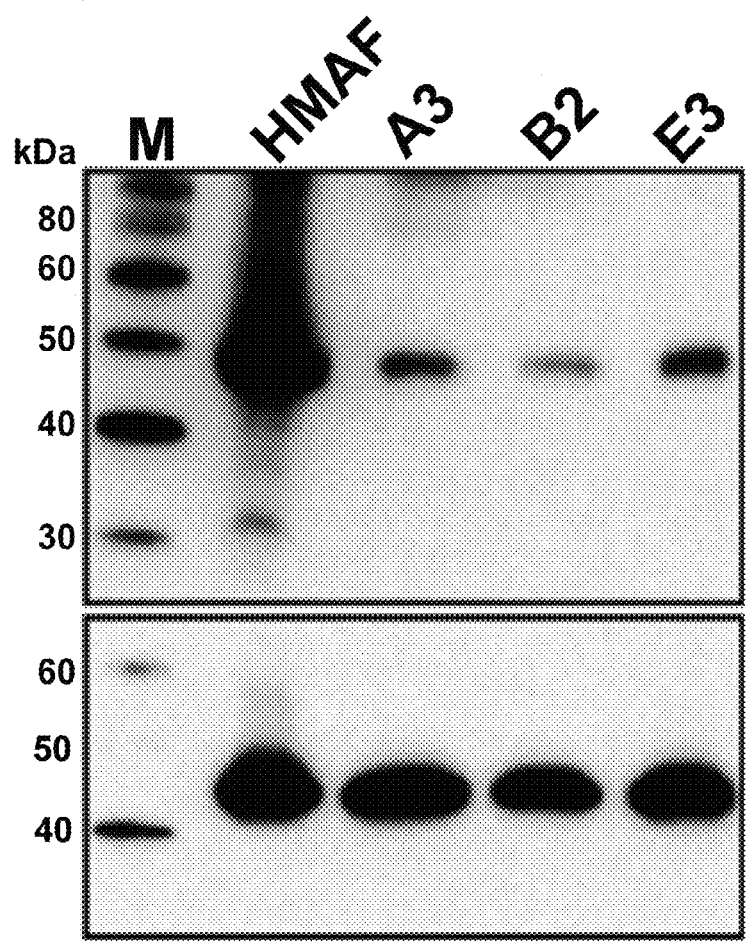

The antigenic specificity of Fabs A3, B2, and E3 was first determined by Western blot analysis using their derived humanized MAbs. A lysate of JEV-infected C6/36 cells (FIG. 3A, upper panel) or a recombinant E preparation (FIG. 3A, lower panel) was separated by SDS-PAGE and then blotted on a nitrocellulose membrane. MAb A3 and E3 bound to E (50 kD and a minor band at 46 kD), but no such binding was detected with MAb B2 under the same conditions. The possibility that MAb B2 reacts with a conformational epitope was investigated further by immunoprecipitation of the cell lysate (FIG. 3B, upper panel) or the recombinant E (FIG. 3B, lower panel) under native conditions, for instance, in the absence of SDS and β-mercaptoethanol. Binding of E by MAbs A3 and E3 was detected in both panels. By comparison, the binding activity of MAb B2 for virion E as well as recombinant E was low but definitely detected, indicating that MAb B2 reacted with native JEV E. All three MAbs failed to precipitate E under reducing conditions.

Example 5

Binding Activities of Fabs and Derived MAbs for JEV

This Example describes the determination of the binding activities of the disclosed Fabs and their respective MAbs as measured by ELISA and SPR. The order of Fab binding affinity for recombinant E was E3>A3>B2 measured by SPR, whereas that for the virion E was B2>A3>E3 by ELISA.

Figure 4A:
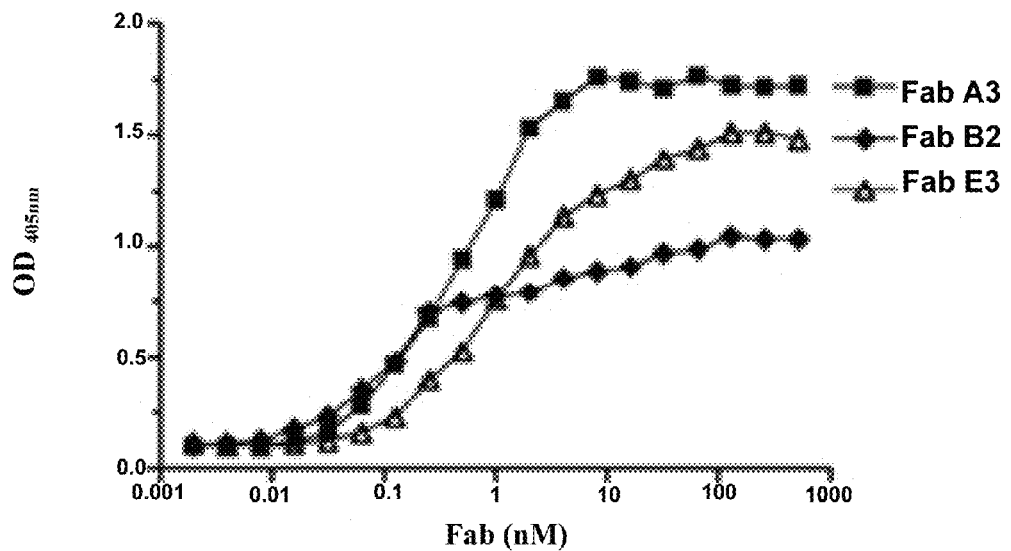
FIGS. 4A-4B are a series of graphs showing the binding activities of JEV Fabs.

The binding activities of Fabs and their derived MAbs for JEV virions in the absence of detergents were determined by ELISA. The concentration of each antibody required to attain 50% maximum binding was calculated by nonlinear regression (FIG. 4A). The concentration provides an estimate of the binding affinity $K_D$. Accordingly, the $K_D$ was 0.45±0.06 nM for Fab A3, 0.28±0.11 nM for Fab B2 and 0.98±0.07 nM for Fab E3 (Table 4). Conversion from the monovalent Fab to the bivalent MAb form increased the antibody avidity 3- to 4-fold. A consistent correlation was observed for each antibody when the $K_D$ value was compared with the neutralization titer (r=0.97).

Figure 4B:
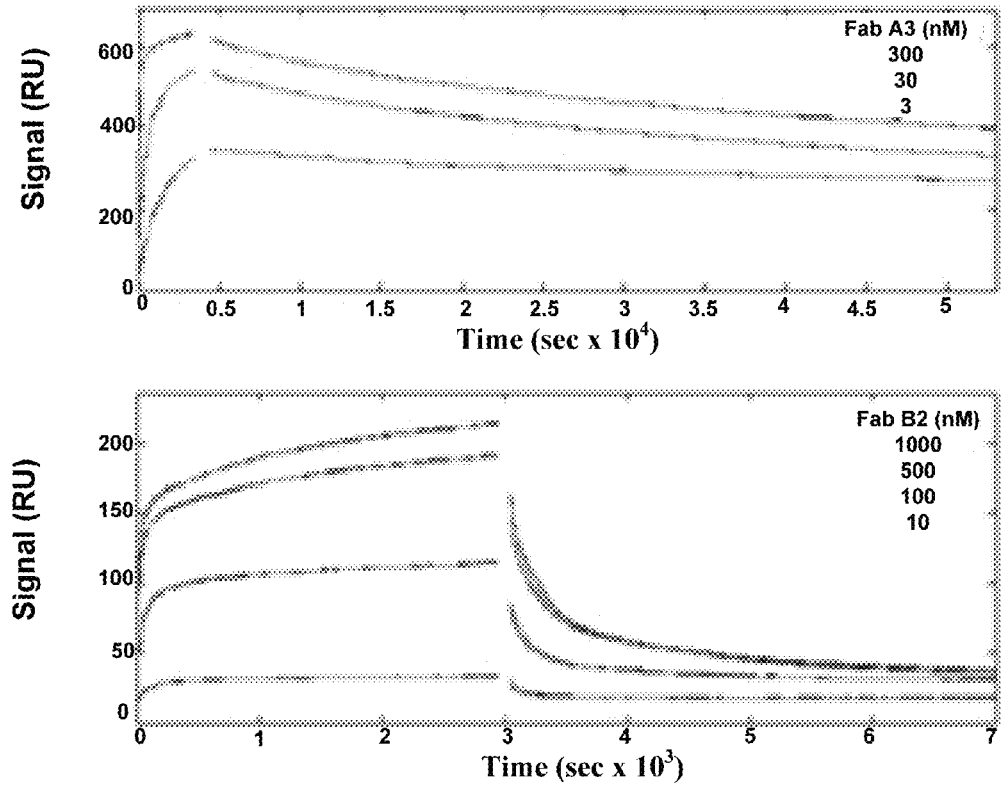

Next, it was determined whether there is a similar correlation between Fab binding affinity for recombinant E and the neutralization potency. SPR measurements allow a precise, real-time determination of Fab-E association and dissociation rates. Representative tracings for Fabs A3 and B2 are shown in FIG. 4B. Using this analysis, the affinity constant $K_d$ measured for Fab A3 was 0.72 nM and that for Fab E3 was 0.35 nM, comparable to the $K_D$ values measured by ELISA (Table 4). Surprisingly, the $K_d$ of Fab B2 for binding to recombinant E was ≥150 fold weaker than that measured for Fab A3 or E3. The $K_d$ of Fab B2 was also significantly weaker than the $K_D$ measured with virions by ELISA (110 nM vs 0.15 nM, respectively). The off-rate of Fab B2 was ≥120-fold faster than that of Fab A3 or E3. The order of Fab binding affinity for recombinant E was E3>A3>B2 measured by SPR, whereas that for the virion E was B2>A3>E3 by ELISA.

Figures 5A, 5B, 5C:
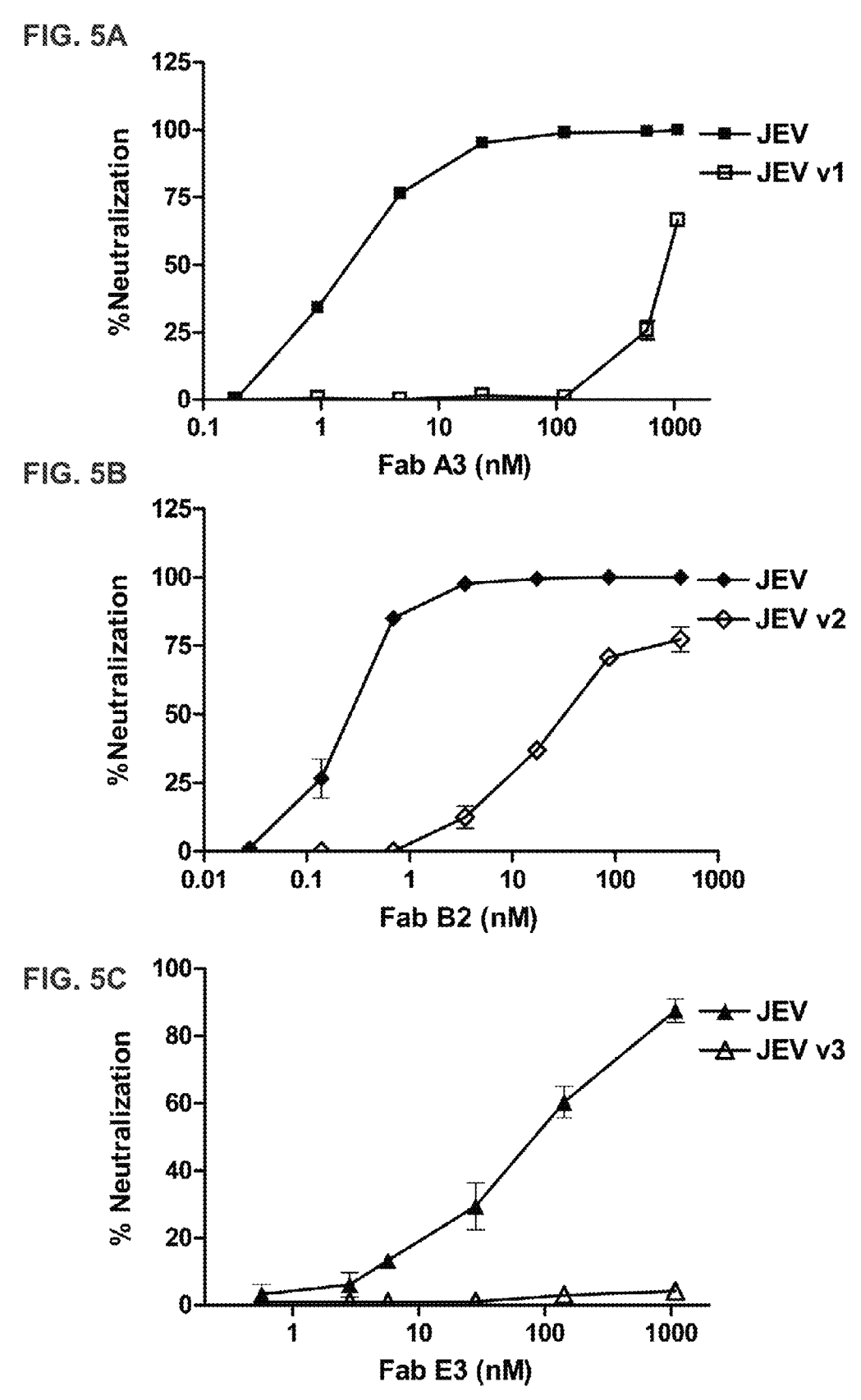

Fabs A3, B2, and E3 were each used to isolate neutralization-escape mutants of JEV SA-14-14-2. Antigenic variant JEV-v1 was isolated from Fab A3, JEV-v2 from Fab B2 and JEV-v3 from Fab E3. When the selecting Fab was used in the neutralization assay, variants JEV-v1 and JEV-v2 showed approximately 340- and 132-fold more resistance than the parental virus, respectively (FIGS. 5A and 5B). JEV-v3 was completely resistant to neutralization by 1080 nM Fab E3 (FIG. 5C).

Figure 6A:
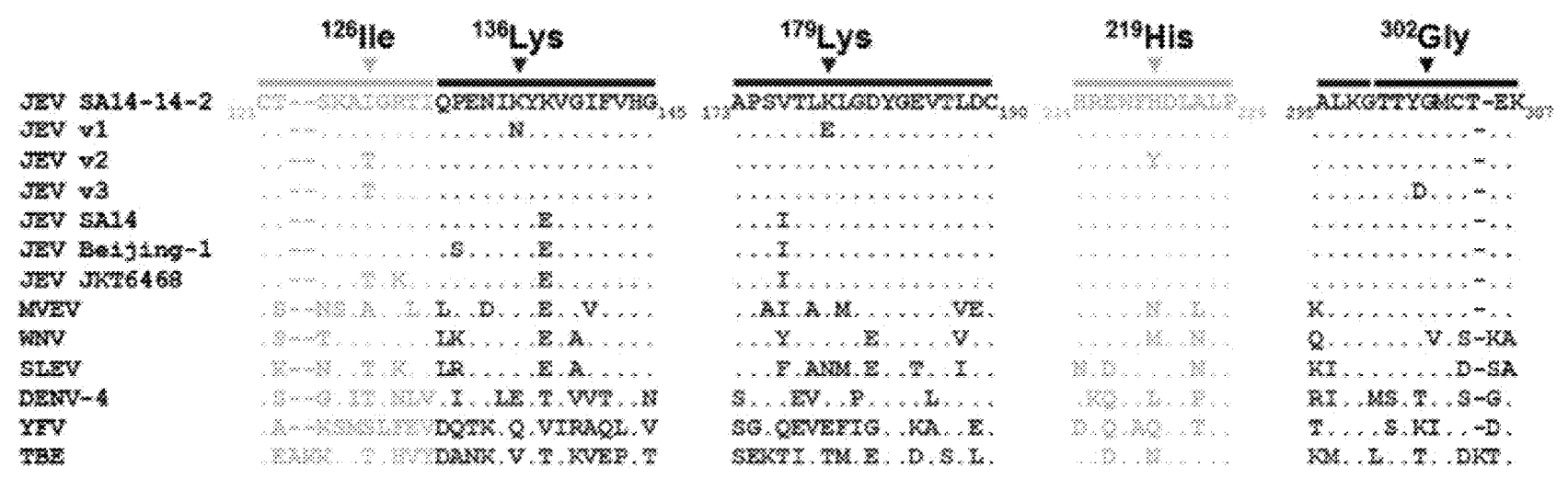
Figure 6B:

To map the epitope determinants of JEV-neutralizing antibodies, the C-prM-E sequences of variants v1, v2 and v3 and the parental virus were determined. FIG. 6A shows the sequence alignment in the regions surrounding the amino acid substitutions in the variants. Variant v1 contained two substitutions in E, $Lys_{136}$-Asn (β-strand $E_0$) and $Lys_{179}$-Glu (β-strand Go), both located in domain I. These two amino acids are conserved, but the surrounding amino acids vary among members of the JE group, which possibly accounts for the lack of reactivity of Fab A3 with WNV by ELISA (Table 2). These amino acids were 20.7 Å apart and exposed on the surface of E, according to the 3-D JEV E protein model based on the WNV E crystal coordinates (FIG. 6B). Variant v2 also contained two substitutions, Helm-Thr (β-strand e) and $Tyr_{219}$-His (α-A), at a distance of 16.2 Å in domain II. Binding of Fab B2 to WNV was not observed, despite the conservation of $Ile_{126}$ and surrounding amino acids (FIG. 6A). Variant v3 also contained two substitutions, $Gly_{302}$Asp in domain III and $Ile_{126}$Thr in domain II. The two positions were approximately 64.6 Å apart and Fab E3 reacted with domain III sequences, indicating that $Ile_{126}$Thr was not responsible for resistance to neutralization by this antibody. Based on the comparison of the escape variant and the wild type virus $PRNT_{50}$ titers, it is possible that there might be other major epitope determinants, especially for Fabs A3 and B2.

Example 7

JEV Recombinant Es Containing Single Amino Acid Substitutions

This Example describes analysis of the effect of mutations on antibody binding. $Lys_{136}$ in domain I, $Ile_{126}$ in domain II,

TABLE 4

Binding and neutralizing activities of Fabs and MAbs

| Antibody | SPR[a] | | | ELISA, KD (nM)[b] | | $PRNT_{50}(nM)$[c] |
|---|---|---|---|---|---|---|
| | kon (M⁻¹ s⁻¹) | koff (s⁻¹) | Kd (nM) | Fab | MAb | |
| A3 | 4.0 × 10⁴ | 2.8 × 10⁻⁵ | 0.72 | 0.45 ± 0.06 | 0.15 ± 0.07 | 2.55 ± 0.42 |
| B2 | 4.2 × 10⁴ | 4.6 × 10⁻³ | 110 | 0.28 ± 0.11 | 0.08 ± 0.03 | 0.25 ± 0.09 |
| E3 | 1.0 × 10⁵ | 3.6 × 10⁻⁵ | 0.35 | 0.98 ± 0.07 | 0.31 ± 0.10 | 84.9 ± 20.2 |

[a]Recombinant E was immobilized on the solid phase, and real-time measurements of Fab binding were made by SPR.
[b]Concentration of Fab or MAb that gave half-maximal binding to JEV virions determined by ELISA.
[c]Concentration of Fab that neutralized 50% of JEV plaques on Vero cells.

Example 6

Localization of Epitope Determinants on E

This Example describes mapping of the epitope determinants of JEV-neutralizing antibodies by determining the C-prM-E sequences of variants v1, v2 and v3 and the parental virus.

and $Gly_{302}$ in domain III are the major epitope determinants of MAbs A3, B2 and E3, respectively.

Figure 7A:
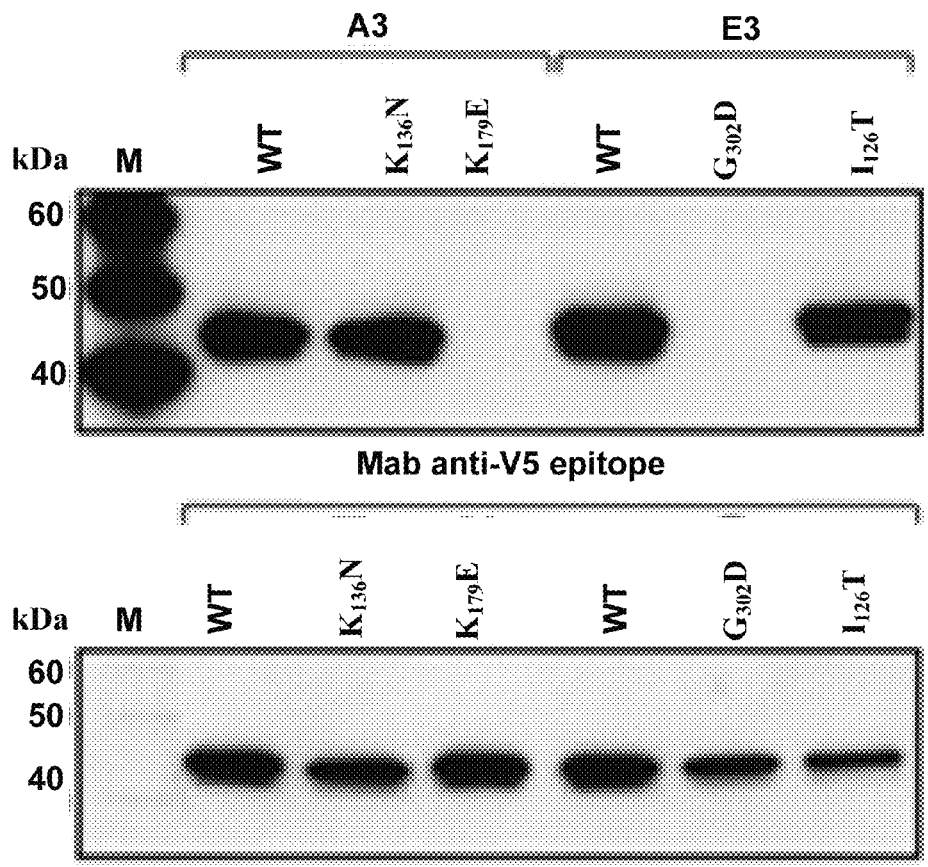
FIGS. 7A-7B are a series of digital images of gels showing the binding analysis of mutant E proteins containing a single substitution at position 126, 136, 179, 219 or 302.

Since there were two mutations in E of each JEV variant (see SEQ ID NO: 10), the effect of each mutation on antibody binding was analyzed. JEV E proteins containing a single substitution of $Ile_{126}$-Thr, $Lys_{136}$-Asn, $Lys_{179}$-Asp, $His_{219}$-Tyr or $Gly_{302}$-Asp were generated Immunoblots showed $Lys_{136}$-Asn substitution had no effect, whereas the $Lys_{179}$-Asp mutation lost reactivity for MAb A3 (FIG. 7A).

Figure 7B:
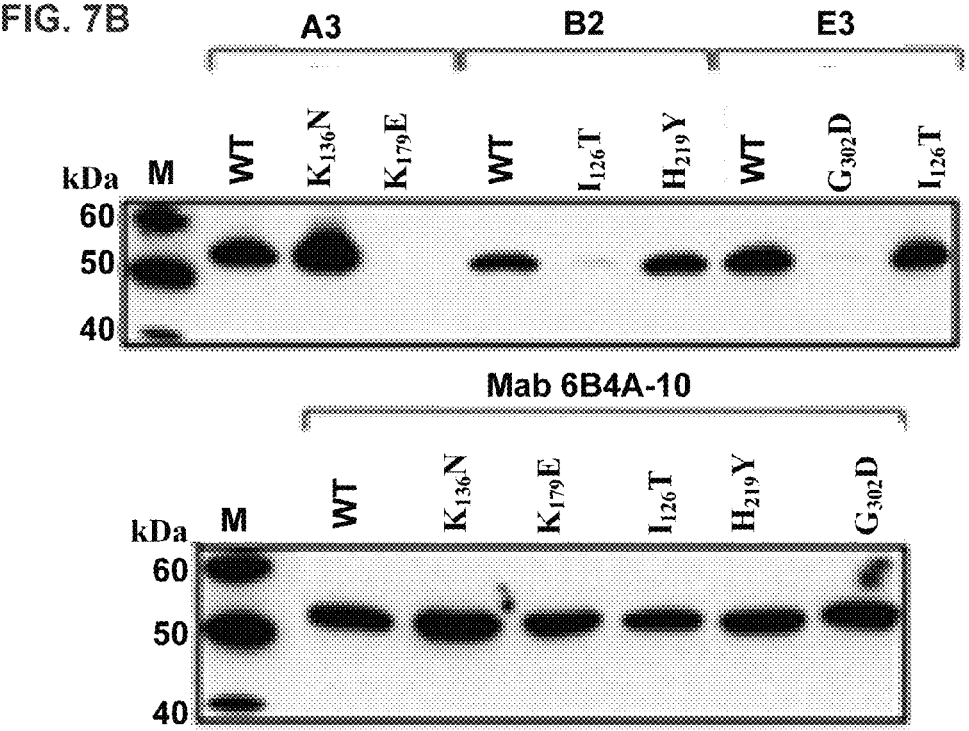

Similarly, Gly$_{302}$-Asp substitution lost reactivity for MAb E3, whereas Ile$_{126}$-Thr had no effect, as predicted. The antibody-binding patterns of these E constructs were also confirmed by immunoprecipitation (FIG. 7B). The latter assay further showed that Ile$_{126}$-Thr substitution lost the reactivity for MAb B2, whereas His$_{219}$-Tyr did not affect binding. As a positive control, mouse MAb 6B4A-10 reacted with all of these mutant E constructs in both assays. These results support the conclusion that Lys$_{136}$ in domain I, Ile$_{126}$ in domain II, and Gly$_{302}$ in domain III are the major epitope determinants of MAbs A3, B2 and E3, respectively.

Example 8

Neutralization of the Attenuated and Wild Type JEV Strains by Fabs and Humanized MAbs This Example describes neutralization of the attenuated JEV strain and the wild type strains representing each genotype by three highly-neutralizing Fabs and humanized MAbs derived from these Fabs.

Earlier the neutralizing titers of Fabs were determined using attenuated JEV strain SA14-14-2 (Genotype III). Three highly-neutralizing Fabs were further evaluated for neutralization of wild type JEV strains representing each of the four genotypes. Each of these Fabs neutralized wild type members of Genotype I-IV as efficiently as the attenuated strain, with the exception that Fab B2, which neutralized strain JKT 9092 (Genotype IV) at a PRNT$_{50}$ titer reduced by greater than $10^3$ fold (Table 5). Fab B2 was the most efficient neutralizer of other strains and Fab E3 was the least efficient. Humanized MAbs derived from these Fabs were also used for neutralization of the attenuated strain and the wild type strains representing each genotype. MAbs A3 and B2 showed a PRNT$_{50}$ titer 3-100 fold higher than that of the Fab counterpart. MAb E3 had a PRNT$_{50}$ titer 40 to >1000 fold higher than that measured for Fab E3 against all genotype strains. JEV JKT 9092, like other strains, was efficiently neutralized by MAb A3 and E3, although it was only moderately neutralized by the highly neutralizing MAb B2.

TABLE 5

Neutralization of JEV strains representing genotypes I to IV by Fabs and humanized MAbs

| Genotype | PRNT$_{50}$ titer (nM)$^a$ of antibody: | | | | | |
|---|---|---|---|---|---|---|
| | A3 | | B2 | | E3 | |
| (strain) | Fab | MAb | Fab | MAb | Fab | MAb |
| I (JE1991) | 1.30 | 0.04 | 0.06 | 0.02 | 53.05 | 0.21 |
| II (JE B1034/8) | 3.47 | 0.04 | 1.85 | 0.02 | 161.74 | 0.14 |
| III (Beijing) | 2.82 | 0.20 | 0.06 | 0.02 | 27.60 | 0.71 |
| III (SA14-14-2) | 2.55 | 0.20 | 0.25 | 0.03 | 84.90 | 0.93 |
| IV (9092) | 1.74 | 0.07 | >2,170 | 2.00 | 22.00 | 0.36 |

$^a$1 nM = ~0.15 μg/ml.

Example 9

Protective Capacity of Humanized MAbs Against JEV Infection in Mice

This Example describes the evaluation of the protective and therapeutic capacity of the humanized MAbs against JEV infection in mice.

Figure 8A:
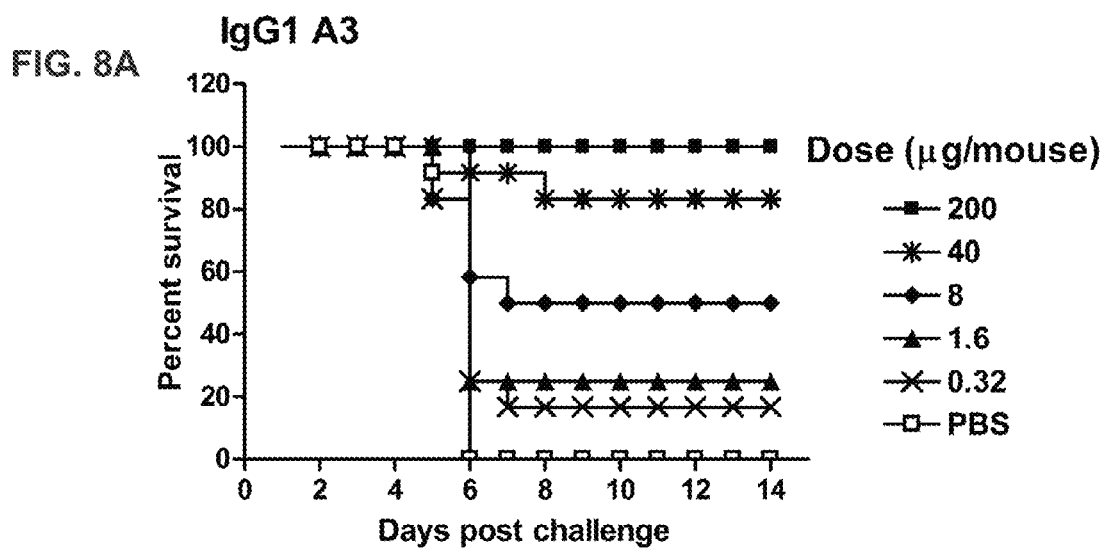
FIGS. 8A-8C are a series of graphs showing the protective activity of humanized JEV IgG1 antibodies (MAbs) using a mouse JEV challenge model. Inbred ddy mice (n=12) were injected i.p. with MAb A3 (FIG. 8A), MAb B2 (FIG. 8B) or MAb E3 (FIG. 8C) at various doses indicated. Un-protected control mice were administrated PBS diluent. 24 hours later mice were infected i.c. with JEV strain.
Figure 8B:
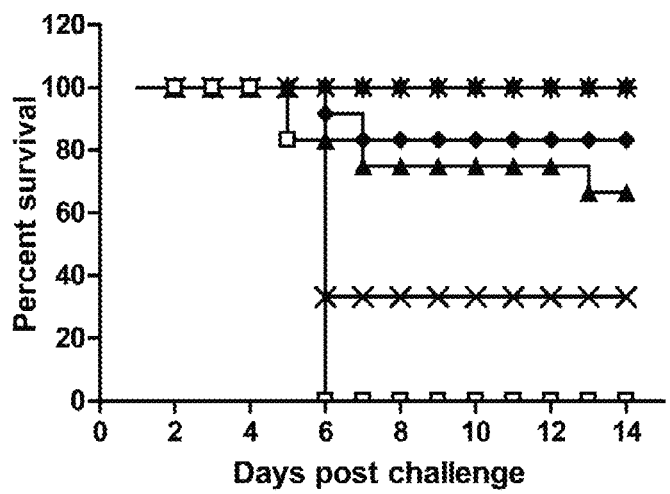
Figure 8C:
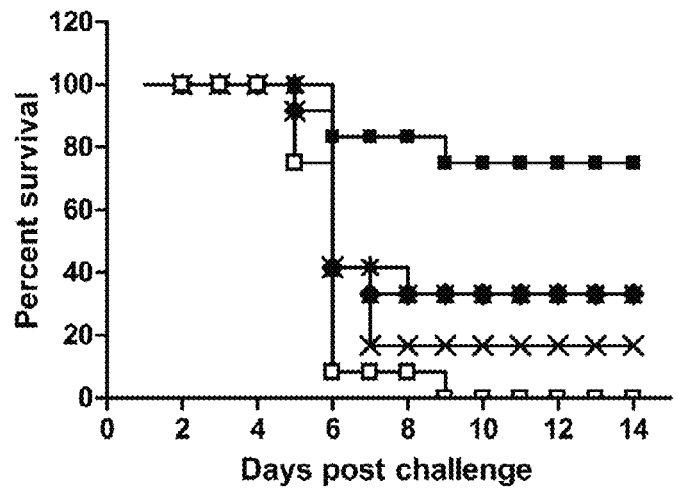

The mouse JEV encephalitis model used for validation of the inactivated JEV vaccine in commercial production was employed to evaluate the protective capacity of humanized MAbs. Four-week-old, inbred ddy mice were each inoculated subcutaneously with a single dose of MAb ranging from 0.32 to 200 μg. Mice were challenged with 40×LD$_{50}$ of JEV strain Nakayama intracerebrally 24 hours later. At a dose of 200 μg/per mouse, Mabs A3 and B2 protected 100% and Mab E3 protected 75% of mice in the groups, compared to no survival in the unprotected group following virus challenge (FIG. 8). Titration of MAbs against virus infection showed a dose-dependent response in terms of the survival rate and average survival time. The 50% protective dose per mouse calculated according to the ordinal-regression model probit was 0.84 μg for MAb B2, 5.8 μg for MAb A3 and 24.7 μg for MAb E3. The protective capacities of these MAbs ranked in the same order as their neutralizing activities in vitro. These experiments confirm the feasibility of neutralizing MAb passive transfer for prevention of JEV encephalitis.

The use of these MAbs for therapy of JEV encephalitis was also investigated. MAb B2 administered at a single dose of 200 μg one day after JEV infection resulted in a 50% survival rate (Table 6). Although fewer survivals were found after similar transfer with the less protective MAb A3 or E3 one day after JEV infection, the average survival time increased significantly with MAb B2 (8.0±1.4 days) or MAb A3 (7.4±0.7 days), compared with 5.9±0.8 days for unprotected animals. Thus, passive transfer with either of these MAbs improved the outcome of JEV infection when administered one day prior to infection (Table 6). However, the average survival time was in the range of 6.2 to 6.3 days for MAb A3 and 5.2 to 6.3 days for MAb B2, not significantly different from 5.8 to 5.9 days for the PBS control group when administrated 3 or 5 days prior to infection.

TABLE 6

Protection by passive transfer of MAb to mice against prior infection with 40x LD$_{50}$ of JEV strain Nakayama 1 day earlier

| MAb | No. survived/no. in group (AST$^a$ ± SD [days]) | P value |
|---|---|---|
| A3 | 3/12 (7.4 ± 0.7) | 0.0001$^b$ |
| B2 | 6/12 (8.0 ± 1.4) | 0.015$^b$ |
| E3 | 3/12 (6.3 ± 1.0) | 0.22 |
| PBS | 0/12 (5.9 ± 0.8) | |

$^a$AST, average survival time.
$^b$The average survival time of the indicated MAb-treated group was significantly different from that of the control group by t test. PBS diluent was used in the group in lieu of MAb. Survival rates were also calculated.

Example 10

Humanized Monoclonal Antibodies Derived from Chimpanzee Fabs Efficient for Neutralization of Japanese Encephalitis Virus (JEV) In Vitro and Protection Against JEV Infection in Mice This example describes the epitopes of the envelope protein bound by monoclonal antibodies, including neutralizing antibodies.

Different panning strategies have served the purpose of recovering a large panel of JEV antibodies reactive with epitopes that mapped to all three domains in E. Fab A3 and three other Fabs that were selected for strong binding to JEV SA14-14-2 virions were highly neutralizing (Table 2). These Fabs appear to represent a major subset of neutralizing antibodies reactive to an immunodominant epitope(s) on JEV. A major determinant of the epitope reactive to Fab A3 mapped to $Lys_{179}$ within a β-strand in domain I of E. $Lys_{179}$ is conserved among JEV strains of different genotypes, indicating the importance of this neutralizing antibody for protection. $Lys_{179}$ of JEV E aligned with $Lys_{174}$ in DENV-4 E. Only a few mouse MAbs that neutralize flaviviruses have been shown to react with epitope determinants that mapped to domain I in E (Holzmann et al., (1997) *J Gen Virol* 78 (Pt 1):31-7; Ryman et al., (1997) *J Gen Virol* 78 (Pt 6):1353-6; Ryman et al., (1997) *Virology* 230:376-80). For example, the epitope determinants of TBEV-neutralizing MAbs i2 and IC3 from mice have been mapped to positions 171 and 181 (corresponding to JEV E position 170 and 180; Holzmann et al., (1997) *J Gen Virol* 78 (Pt 1):31-7). These results demonstrate that a cluster of epitopes involving the antigenic determinant $Lys_{179}$ in JEV E (or the corresponding $Lys_{174}$ in DENV-4 E) apparently shared between rodents and primates (chimpanzees and possibly humans), play an important role in inducing flavivirus type-specific antibodies.

The epitope-masking, followed by panning, has allowed the recovery of Fab B2 and two other related antibodies (Fabs F1 and F3) with high neutralizing titers against JEV in vitro. Sequence analysis of Fab B2 neutralization-escape variant v2 identified $Ile_{126}$ within the small loop between d and e β-strands in domain II. Evidence for epitope determinant $Ile_{126}$ is also supported by the demonstration that substitution of $I_{126}T$ in recombinant 80% E truncated at the C-terminus resulted in loss of binding for MAb B2. Epitopes that are closely related to this d-e loop epitope in domain II have been described for mouse antibodies against JEV or other flaviviruses by analysis of antigenic variants (Hasegawa et al., (1992) *Virology* 191:158-65; Holzmann et al., (1997) *J Gen Virol* 78 (Pt 1):31-7; McMinn et al., (1995) *Virology* 211:10-20; Morita et al., (2001) *Virology* 287:417-26). For example, antigenic variants partially resistant to mouse JEV-neutralizing MAb 503 were found to contain mutations at $Ile_{126}$ (domain II), $Lys_{136}$ (domain I) or $Ser_{275}$ (domain II) in E clustered at the junction of domains I and II. Presumably, some of these amino acids are contact residues for this MAb. Thus, the epitope reactive to MAb 503 appears to consist of discontinuous sequences involving an important determinant at $Ile_{126}$ (Morita et al., (2001) *Virology* 287:417-26). These observations suggest that these chimpanzee and mouse neutralizing MAbs react with similar or overlapping epitopes, probably involving a common determinant at or near position 126.

It is clear that JEV virions can select strongly-neutralizing antibodies reactive to domain I- and II-specific epitopes. Two domain III-reactive Fabs were also recovered with the use of domain III-specific recombinant E. One of these (Fab E3) had a moderate neutralizing activity in vitro and its epitope determinant mapped to JEV-conserved $Gly_{302}$ within the N-terminal segment of domain III (amino acid residues 302-309). Further, Fab E3 competed with the binding of mouse MAb E3.3, which recognizes a conformation-dependent epitope in E domain III (Wu et al., (2003) *J Biol Chem* 278:46007-13). It has been reported that the most potent flavivirus neutralizing antibodies recognize epitopes on the upper lateral surface of domain-III, composed of residues of the amino-terminal region and the three loops FG, BC and DE (Nybakken et al., (2005) *Nature* 437:764-9; Sukupolvi-Petty et al., (2007) *J. Virol* 81:12816-26; Wu et al., (2003) *J Biol Chem* 278:46007-13). Highly neutralizing antibodies that recognize sequences in domain III were not recovered from the chimpanzee antibody library. This apparent lack of immunodominance of domain III antibodies was not surprising in view of experience with neutralizing antibodies from DENY-infected chimpanzees and the recent characterization of human antibodies against WNV (39, Throsby et al., (2006) *J Virol* 80:6982-92). However, it can not be ruled out that JEV virions or the recombinant domain III E protein coated on the plate had not assumed the native conformation for binding to highly neutralizing antibodies.

Recent studies with DENY, WNV and TBEV suggest that a major subset of broadly cross-reactive antibodies are directed against immunodominant epitopes that include the fusion peptide in the E protein (Goncalvez et al., (2004) *J Virol* 78:12919-28; Stiasny et al., (2006) *J Virol* 80:9557-68; Throsby et al., (2006) *J Virol* 80:6982-92). Without being bound by theory, the most plausible explanation for the lack of such antibodies described herein is that SA14-14-2 virus used for panning binds weakly to the cross-reactive antibodies, thereby preventing their isolation. The $Phe_{107}Leu$ substitution in the E fusion loop alone was responsible for reduced binding affinity of SA 14-14-2 virions to the broadly cross-reactive chimpanzee MAb 1A5 (Goncalvez et al., (2004) *J Virol* 78:12919-28).

ELISA provided useful insights into Fab binding activities for JEV virions. Highly-neutralizing Fabs B2 and A3 reached half maximum binding at approximately 0.5 nM and ~10 nM respectively, whereas the comparable value for moderately-neutralizing Fab E3 was ~100 nM (FIG. 4A). The concentration for half-maximum binding, together with the $PRNT_{50}$ titers allowed measurement of antibody neutralization potency, based on the calculation of the threshold occupancy of accessible antibody sites on the virion (Pierson et al., (2007) *Cell Host & Microbe* 1:135-145). According to the multiple-hit theory and stoichiometric analysis of epitope occupancy for neutralization (Klasse et al., (2002) *J Gen Virol* 83:2091-108), the most potent antibodies neutralize the virus at concentrations with low occupancy of the epitopes available for binding on the virion. The occupancy for the most potent JEV-neutralizing MAb B2 was approximately 28% of available sites, whereas the occupancy for MAbs A3 and E3 were calculated at 45% and 66% of the accessible sites, respectively. The three JEV-neutralizing antibodies bind to specific epitopes in three separate E domains and most probably neutralize the virus by different mechanisms. Other contributing factors for assessment and interpretation of the antibody binding stoichiometry likely also include the epitope presentation of antigen preparations. To that effect, the binding affinity of Fab B2 for the recombinant E protein measured by SPR was very different from that determined for the virion by ELISA, for instance, Kd of 110 nM vs $K_D$ of 0.28 nM (Table 4). One possible explanation is the conformational dependency of the B2 epitope, as shown by the loss of MAb B2 binding to the recombinant E or the virion in a Western blot assay. Accordingly, the number of accessible sites for B2 binding differed between the recombinant E and the virion on a molar basis. The high neutralization potency of MAb B2 could be partially determined by a higher affinity for a limited subset of E protein conformations that most closely mimic E on the viral surface.

The presently recognized four JEV genotypes show a 7% or greater nucleotide sequence divergence based on limited sequences (Chen et al., (1992) *Am J Trop Med Hyg* 47:61-9; Solomon et al., (2003) *J Virol* 77:3091-8). Strains of genotype IV are the least similar and probably represent the ancestral lineage with up to 20% nucleotide and 6.5% amino acid divergence compared to other genotype strains. Genotypes I-III are most wide-spread and responsible for epidemic disease. As demonstrated herein, each of the three Fabs and derived humanized MAbs exhibits a high neutralizing activity against a broad spectrum of JEV genotype strains. One single exception is that the neutralizing activity of MAb B2 against JEV strain 9092 (genotype IV) was reduced by approximately 100 fold, compared to that against other genotype strains. A sequence search of strain 9092 (accession # U70409) in the data base revealed that the substitution of $Ile_{126}Thr$ identified earlier in the B2 escape mutant was not present. This observation suggests the possibility that other mutations in E of the JEV strain affecting MAb B2 binding and neutralization are present in this one strain. A sequence analysis of other genotype IV strains revealed the presence of the $Ile_{126}Thr$ substitution in strains JKT 6468 (accession # AY184212) and JKT 7003 (accession #70408) in E, indicating that both JEV strains can exhibit resistance to neutralization by MAb B2. Strains of genotype IV were all isolated in 1980-1981 from mosquitoes and are believed to have remained in the Indonesia-Malaysia region; this substitution could be limited to these strains.

Unlike JEV genotype IV strains, strains of genotypes I-III have spread widely in Asia in recent years Immunization using the inactivated or live SA14-14-2 JEV vaccine, both prepared from genotype III strains, has effectively controlled JE epidemics in most countries. However, JEV outbreaks remain a public health problem for residents in the regions where JEV vaccination is inadequate and a concern for travelers to these regions as well. Antibody-mediated prevention of JEV infection is an alternative to vaccines. Demonstration of passive protection with humanized chimpanzee MAbs against JEV infection in vivo is provided herein. The 50% protective dose ($ED_{50}$) was measured for MAbs B2 (0.32 μg), A3 (5.8 μg) and E3 (24.7 μg) for 21-g mice. It is evident that JEV-protective efficacies in vivo correlate well with neutralizing activities in vitro. Administration of 200 μg/mouse of MAb B2 one day after lethal intracerebral JEV infection protected 50% of mice, whereas all mice in the control group died. A significant improvement of JEV infection survival time after administration of MAbs B2 and A3 was also evident. Thus, these MAbs are therapeutically effective.

In contrast, the average survival time was not prolonged when mice were inoculated with any of the antibodies three or five days after JEV challenge. Virus titers can reach $\sim 1 \times 10^7$ to $1 \times 10^8$ FFU/g in the brain of 3-week-old mice three to five days after intracerebral inoculation of JEV (Kuhn et al., (2002) *Cell* 108:717-25). Other mouse JE encephalitis models employing less severe intraperitoneal inoculation have also been described (Jan et al., (1993) *Am J Trop Med Hyg* 48:412-23; Kimura-Kuroda & Yasui (1988) *J Immunol* 141:3606-10). Studies have shown that inoculation of 200 μg of mouse MAb 503 on day 5 after intraperitoneal challenge protected 82% of the animals (Kimura-Kuroda & Yasui (1988) *J Immunol* 141:3606-10). Passive protection on three or five days after infection by our humanized antibodies would probably have been possible if the virus were introduced into the animals intraperitoneally. However, the test used herein (by challenging mice intracerebrally) was a more stringent test of protection. Infection intervention could be further improved by the combined use of two or more Mabs, such as B2 and A3, which react to separate domains and possibly neutralize the virus by different mechanisms.

Example 11

Neutralization Synergy of Humanized JEV MAbs In Vitro

This Example evaluates neutralization synergy of humanized JEV MAbs for attenuated JEV strain SA-14-14-2.

Earlier the neutralizing titers of individual MAbs were determined using attenuated JEV strain SA-14-14-2 (Example 8). The level of neutralization enhancement observed in vitro when combining neutralizing JEV MAbs A3, B2, and/or E3, was determined using two different approaches.

First, a classical approach was used, in which the MAbs were mixed at a fixed (constant) ratio determined on the basis of their relative neutralization potency (50% plaque reduction neutralization test, $PRNT_{50}$). Dose-response curves were determined for the antibody mixture (combination) and for each of the individual antibodies in the mixture. The presence or absence of neutralization synergy was assessed by comparing the $PRNT_{50}$ values for each of the individual antibodies to the antibody mixture. No synergy was evident by comparison of the $PRNT_{50}$ of each of the individual antibodies (A3, B2, or E3) as compared to the values of the double (A3 and B2; B2 and E3; or A3 and E3) or triple (A3 and B2 and E3) JEV MAb combination (Table 7).

TABLE 7

Neutralization of JEV SA-14-14-2 by MAbs alone or in combination[a].

| Antibody | $PRNT_{50}$ (μg/ml)[b] |
|---|---|
| A3 | 0.04 |
| B2 | 0.005 |
| E3 | 0.09 |
| A3:B2 (1:1) | 0.008 |
| A3:E3 (1:1) | 0.03 |
| B2:E3 (1:1) | 0.006 |
| A3:B2:E3 (1:1:1) | 0.006 |

[a]Neutralization synergy of antibody combinations for JEV SA-14-14-2 were determined using a dose-response curves for each of the antibodies alone and for antibody combinations mixed in an equimolar ratio.
[b]$PRNT_{50}$ were calculated by estimating the 50% neutralization titer from the neutralization curves.

A second approach with a variable antibody ratio was also used to determine neutralization synergy of the JEV MAbs in vitro using attenuated JEV strain SA14-14-2. In this approach, one antibody in the combination was titrated and a fixed amount of a second neutralizing antibody at a weakly neutralizing concentration was added. The presence of neutralization enhancement was assessed by comparing the $PRNT_{50}$ values of the combination antibody mixture to those obtained with a single antibody titration. An enhancement of neutralization was determined as a significant increase of the titration curve of the antibody mixture compared to the titration curve of the first antibody alone. The results shown in Table 8 for neutralization of JEV SA-14-14-2 with MAbs A3, B2, or E3, and their combinations confirm the results shown in Table 7. The mixing of MAbs A3, B2, or E3 in all possible two antibody combinations did not alter the neutralization titer observed. Thus, a combination of humanized JEV MAbs did not improve upon the neutralization titers observed for the corresponding individual humanized JEV MAb titers (Tables 7 and 8).

TABLE 8

Neutralization of JEV SA-14-14-2 by MAbs alone or in combination[a].

| | $PRNT_{50}$ (μg/ml) of MAb 1 or in combination with MAb 2[c] | | |
|---|---|---|---|
| MAb 2 (μg/ml)[b] | A3 | B2 | E3 |
| None | 0.04 | 0.005 | 0.09 |
| A3 (0.03) | — | 0.008 | 0.11 |

TABLE 8-continued

Neutralization of JEV SA-14-14-2 by MAbs alone or in combination[a].

| MAb 2 (μg/ml)[b] | PRNT$_{50}$ (μg/ml) of MAb 1 or in combination with MAb 2[c] | | |
|---|---|---|---|
| | A3 | B2 | E3 |
| B2 (0.004) | 0.05 | — | 0.06 |
| E3 (0.1) | 0.03 | 0.005 | — |

[a]Neutralization synergy of antibody combinations for JEV SA14-14-2 were determined using the neutralization dose-response curve of MAb 1 in the presence or absence of a fixed, weakly neutralizing concentration of MAb 2.
[b]The fixed concentration of MAb 2 is indicated in parenthesis and represents a weak neutralizing concentration.
[c]PRNT$_{50}$ of MAb 1 is shown alone or in combination with a weakly neutralizing concentration of MAb 2.

Example 12

Protective and Therapeutic Capacity of Humanized MAb Combinations Against JEV Infection in Mice This example describes the evaluation of the protective and therapeutic capacity of the humanized MAb combination (A3 and B2) against JEV infection in mice.

The mouse JEV encephalitis model used for validation of the inactivated JEV vaccine in commercial production was employed to evaluate the therapeutic capacity of the humanized MAb combination. Groups of 4-week-old inbred ddy mice (either sex, n=12) were each challenged via the intracerebral (i.c.) route with a diluent containing 40×50% lethal dose (LD$_{50}$) (1.5 FFU) of JEV strain Nakayama in 30 μl. One or two days later, mice were infused with 0.5 ml (20 μg, 100 μg or 200 μg per mouse) of MAbs A3 or B2 alone, or in combination by intraperitoneal (i.p.) route; the control group received PBS diluent only. The mice were monitored daily for clinical signs of infection, including ruffled hair, hunched back, paralysis, and death. When signs of encephalitic paralysis developed, mice were euthanized as the experiment end point. A Student's t test was used to compare the average survival times (AST) between the mouse groups that received a single MAb with those that received a combination of MAbs. At a dose of 200 μg/per mouse, MAb B2 protected 33% of mice in the group, compared to no survivals in the unprotected group following MAb administration (Table 9). A dose of 20 μg/per mouse MAb A3 or 100 μg/per mouse MAb A3 failed to protect any mice in these groups following MAb administration.

The use of these MAb combinations for therapy of JEV encephalitis was also investigated. MAb B2 administered at a single dose of 200 μg 1 day after JEV infection resulted in a 33% survival rate (Table 9). A slight increase in the survival rate (41.7%) was found after transfer of a combination of MAbs B2 and A3 at a ratio of 2:1, 1 day after JEV infection. However, the average survival time (AST) of this group was not significantly different from the group that received PBS (7.1±0.4 days vs. 7.0±0 days; P>0.5, t test) or MAb B2 alone (7.1±0.4 days vs. 10.8±5.5 days; P>0.05, t test). Thus, passive transfer of a combination of MAbs B2 and A3 at a ratio of 2:1 or 10:1 one day after virus challenge did not improve the outcome of JEV infection when compared with the group that received MAb B2 alone (Table 9). Nevertheless, for an effective immunotherapy and/or immunoprophylaxis in humans, a combination of JEV-neutralizing, non-competing MAbs might be required for control of potential neutralization escape mutants and coverage of different strains of JEV.

TABLE 9

Protection by passive transfer of MAb to mice against prior infection with 40× LD$_{50}$ of JEV strain Nakayama 1 day after challenge.

| MAb (μg/mouse) | No. Survived/no. in group (AST[a] ± SD [days]) |
|---|---|
| B2(200) | 4/12 (10.8 ± 5.5) |
| B2(200):A3(100) | 5/12 (7.1 ± 0.4) |
| A3(100) | 0/12 (7.3 ± 0.5) |
| B2(200):A3(20) | 3/12 (7.8 ± 0.7) |
| A3(20) | 0/12 (7.0 ± 0) |
| PBS | 0/12 (7.0 ± 0) |

[a]AST, average survival time.
PBS diluent was used in the control group.

This disclosure provides humanized monoclonal antibodies specific for JEV. The disclosure further provides methods of treating, preventing, or ameliorating JEV infection. It will be apparent that the precise details of the methods described can be varied or modified without departing from the spirit of the described disclosure. We claim all such modifications and variations that fall within the scope and spirit of the claims below.

The invention claimed is:

1. An isolated humanized monoclonal antibody that specifically binds Japanese encephalitis virus envelope protein with a binding affinity of about 1.0 nM or less, wherein the monoclonal antibody comprises a heavy chain and a light chain, wherein the monoclonal antibody comprises one of:
(a) a heavy chain comprising amino acids 31-35 of SEQ ID NO: 1, amino acids 50-66 of SEQ ID NO: 1, and amino acids 96-107 of SEQ ID NO: 1 and a light chain comprising amino acids 24-34 of SEQ ID NO: 4, amino acids 50-56 of SEQ ID NO: 4, and amino acids 89-96 of SEQ ID NO: 4;
(b) a heavy chain comprising amino acids 32-36 of SEQ ID NO: 2, amino acids 50-67 of SEQ ID NO: 2, and amino acids 100-113 of SEQ ID NO: 2 and a light chain comprising amino acids 24-34 of SEQ ID NO: 5. amino acids 50-56 of SEQ ID NO: 5, and amino acids 89-96 of SEQ ID NO: 5; or
(c) a heavy chain comprising amino acids 30-37 of SEQ ID NO: 3, amino acids 52-67 of SEQ ID NO: 3, and amino acids 100-112 of SEQ ID NO: 3 and a light chain comprising amino acids 22-33 of SEQ ID NO: 6, amino acids 49-55 of SEQ ID NO: 6, and amino acids 88-95 of SEQ ID NO: 6,
and wherein the monoclonal antibody further comprises an Fc region of a human IgG$_1$, IgG$_2$, IgG$_3$ or IgG$_4$.

2. The isolated humanized monoclonal antibody of claim 1, wherein the Fc region is a human IgG$_1$ Fc region.

3. The isolated humanized monoclonal antibody of claim 1, wherein the Fc region of the monoclonal antibody has reduced binding to an Fcγ receptor class I binding site as compared to a native Fc region.

4. The isolated humanized monoclonal antibody of claim 3, wherein the Fc region comprises a $C_H2$ domain and/or a $C_H3$ domain, and wherein the antibody has a deletion of four to ten amino acids of the N-terminus of the $CH_2$ domain of the Fc region as compared to a native Fc region.

5. The isolated humanized monoclonal antibody of claim 4, wherein the native Fc region comprises the amino acid sequence of SEQ ID NO: 11.

6. The isolated humanized monoclonal antibody of claim 4, wherein the amino acid sequence of LLGG (SEQ ID NO: 12) is deleted from the $CH_2$ domain of the native Fc region.

7. The isolated humanized monoclonal antibody of claim 6, wherein the amino acid sequence of any one of SEQ ID NOs: 13-30 is deleted from the $CH_2$ domain of the native Fc region.

8. The isolated humanized monoclonal antibody of claim 4, wherein the heavy chain of the antibody comprises one of SEQ ID NO: 1, SEQ ID NO: 2, or SEQ ID NO: 3, or an antigen binding fragment of the isolated humanized monoclonal antibody.

9. The isolated humanized monoclonal antibody of claim 4, wherein the light chain of the antibody comprises one of SEQ ID NO: 4, SEQ ID NO: 5, or SEQ ID NO: 6, or an antigen binding fragment of the isolated humanized monoclonal antibody.

10. The isolated humanized monoclonal antibody of claim 4, wherein
    (a) the heavy chain of the antibody comprises SEQ ID NO: 1 and the light chain of the antibody comprises SEQ ID NO: 4;
    (b) the heavy chain of the antibody comprises SEQ ID NO: 2 and the light chain of the antibody comprises SEQ ID NO: 5, or an antigen binding fragment of the isolated humanized monoclonal antibody; or
    (c) the heavy chain of the antibody comprises SEQ ID NO: 3 and the light chain of the antibody comprises SEQ ID NO: 6, or an antigen binding fragment of the isolated humanized monoclonal antibody.

11. The isolated humanized monoclonal antibody of claim 1, wherein the antibody specifically binds to $Lys_{179}$ within a β-strand in domain I of the envelope protein.

12. The isolated humanized monoclonal antibody of claim 1, wherein the antibody specifically binds $Ile_{126}$ within the small loop between d and e β-strands in domain II of the envelope protein.

13. The isolated humanized monoclonal antibody of claim 1, wherein the antibody or antigen-binding fragment thereof is labeled.

14. The isolated human monoclonal antibody of claim 13, wherein the label is a fluorescence, magnetic, enzymatic, or radioactive label.

15. The isolated human monoclonal antibody of claim 13, wherein the label is fluorescein, fluorescein isothiocyanate, rhodamine, 5-dimethylamine-1-napthalenesulfonyl chloride, phycoerythrin, lanthanide phosphors, green fluorescent protein (GFP), Yellow fluorescent protein (YFP), horseradish peroxidase, β-galactosidase, luciferase, alkaline phosphatase, glucose oxidase, avidin, biotin, gadolinium, a lanthanide, $^3H$ $^{14}C$ $^{15}N$ $^{35}s$ $^{90}y$, $^{99}Tc$, $^{111}In$, $^{125}I$, or $^{131}I$.

16. The isolated humanized monoclonal antibody of claim 1, wherein the antibody is conjugated to an immunotoxin or a chemotherapeutic agent.

17. A composition comprising the humanized monoclonal antibody of claim 1 and a pharmaceutically acceptable carrier.

18. A nucleic acid molecule encoding the humanized monoclonal antibody of claim 1.

19. An expression vector comprising the nucleic acid molecule of claim 18, operably linked to a promoter.

20. A host cell transformed with the expression vector of claim 19.

21. A method of treating a subject diagnosed with a Japanese Encephalitis Virus (JEV) infection or at risk for developing a JEV infection, comprising:
    administering to the subject a therapeutically effective amount of the composition of claim 16, thereby treating the subject diagnosed with the JEV infection or at risk for developing the JEV infection.

22. The method of claim 21, wherein the composition is administered intravenously or intramuscularly.

23. A method of detecting a Japanese Encephalitis Virus (JEV) infection in a subject, comprising:
    contacting a sample from the subject with the isolated humanized monoclonal antibody of claim 1; and
    detecting binding of the humanized monoclonal antibody to the sample,
    wherein an increase in binding of the humanized monoclonal antibody to the sample as compared to binding of the humanized monoclonal antibody to a control sample detects the JEV infection in the subject.

24. A method of confirming a diagnosis of a Japanese Encephalitis Virus (JEV) infection in a subject, comprising:
    contacting a sample from a subject diagnosed with the JEV infection with the isolated humanized monoclonal antibody of claim 1; and
    detecting binding of the humanized monoclonal antibody to the sample,
    wherein an increase in binding of the humanized monoclonal antibody to the sample as compared to binding of the humanized monoclonal antibody to a control sample confirms the diagnosis of the JEV infection in the subject.

* * * * *